(12) United States Patent
MacPherson et al.

(10) Patent No.: US 11,976,273 B2
(45) Date of Patent: May 7, 2024

(54) DNA DISPLAY OF FOLDED RNA LIBRARIES ENABLING RNA-SELEX WITHOUT REVERSE TRANSCRIPTION

(71) Applicant: BRANDEIS UNIVERSITY, Waltham, MA (US)

(72) Inventors: Iain S. MacPherson, Honolulu, HI (US); Isaac J. Krauss, Waltham, MA (US)

(73) Assignee: Brandeis University, Waltham, MA (US)

( * ) Notice: Subject to any disclaimer, the term of this patent is extended or adjusted under 35 U.S.C. 154(b) by 469 days.

(21) Appl. No.: 16/486,248

(22) PCT Filed: Feb. 19, 2018

(86) PCT No.: PCT/US2018/018634
§ 371 (c)(1),
(2) Date: Aug. 15, 2019

(87) PCT Pub. No.: WO2018/152470
PCT Pub. Date: Aug. 23, 2018

(65) Prior Publication Data
US 2020/0002699 A1 Jan. 2, 2020

Related U.S. Application Data

(60) Provisional application No. 62/460,365, filed on Feb. 17, 2017.

(51) Int. Cl.
*C12N 15/11* (2006.01)
*C12N 9/12* (2006.01)
*C12N 15/10* (2006.01)
*C12Q 1/6811* (2018.01)

(52) U.S. Cl.
CPC ....... *C12N 15/1048* (2013.01); *C12N 9/1252* (2013.01); *C12Q 1/6811* (2013.01)

(58) Field of Classification Search
CPC ................ C12Q 1/6811; C12N 15/115; C12N 2310/16; C12N 15/1068; C12N 15/1048; C12N 15/111; C12N 2320/13; C40B 30/04
See application file for complete search history.

(56) References Cited

U.S. PATENT DOCUMENTS

| 5,270,163 A | 12/1993 | Gold et al. |
| 2013/0052652 A1 | 2/2013 | Schneider et al. |
| 2016/0076021 A1* | 3/2016 | Stojanovic ......... C12N 15/1048 506/9 |

FOREIGN PATENT DOCUMENTS

WO 2016134521 A1 9/2016

OTHER PUBLICATIONS

International Search Report and Written Opinion for corresponding PCT Application No. PCT/US2018/018634 (dated May 8, 2018).
MacPherson et al., "DNA display of folded RNA libraries enabling RNA-SELEX without reverse transcription," Chem. Commun., 52(19)2878-2881 (2017).
Dua et al., "Patents on SELEX and Therapeutic Aptamers," Recent Patents on DNA & Gene Sequences 2:172-186 (2008).
Renders et al., "A Method for Selecting Modified DNAzymes Without the Use of Modified DNA as a Template in PCR," Chem. Commun. 51:1360-1362 (2015).
Parlea et al., "Cellular Delivery of RNA Nanoparticles," ACS Comb. Sci. 18:527-547 (2016).
Sigma-Aldrich, "Melting Temperature" (2004).

* cited by examiner

*Primary Examiner* — Dana H Shin
(74) *Attorney, Agent, or Firm* — Karen A. LeCuyer; DeWitt LLP

(57) ABSTRACT

The present invention is directed to the method for selecting an RNA molecule that binds to a target molecule and a kit for carrying out the method. This method includes: providing a pool of oligonucleotide complexes that each comprise a ds-DNA molecule and an RNA molecule, the ds-DNA molecule comprising a first DNA strand at least partially annealed to a first region of the RNA molecule, whereby a second region of the RNA molecule is free to adopt a secondary structure; exposing the pool to a target molecule and allowing the second region of the RNA to bind the target molecule; and selecting from the pool one or more oligonucleotide complexes comprising an RNA molecule having the second region bound to the target molecule.

14 Claims, 11 Drawing Sheets

Specification includes a Sequence Listing.

SEQUENCE LISTING

<160> NUMBER OF SEQ ID NOS: 36

<210> SEQ ID NO 1
<211> LENGTH: 21

```
<212> TYPE: DNA
<213> ORGANISM: Artificial
<220> FEATURE:
<223> OTHER INFORMATION: Capture Strand 5' Sequence

<400> SEQUENCE: 1
gctcgttctc cttccctctc c                                                 21

<210> SEQ ID NO 2
<211> LENGTH: 25
<212> TYPE: RNA
<213> ORGANISM: Artificial
<220> FEATURE:
<223> OTHER INFORMATION: Clone 1 thrombin binding sequence

<400> SEQUENCE: 2
uguuacucac aaaauagcga agacu                                             25

<210> SEQ ID NO 3
<211> LENGTH: 25
<212> TYPE: RNA
<213> ORGANISM: Artificial
<220> FEATURE:
<223> OTHER INFORMATION: Clone 2 thrombin binding sequence

<400> SEQUENCE: 3
ccggcgucac aagauagaca aaacu                                             25

<210> SEQ ID NO 4
<211> LENGTH: 25
<212> TYPE: RNA
<213> ORGANISM: Artificial
<220> FEATURE:
<223> OTHER INFORMATION: Clone 3 thrombin binding sequence

<400> SEQUENCE: 4
cgggacucac aagauagaca auacu                                             25

<210> SEQ ID NO 5
<211> LENGTH: 25
<212> TYPE: RNA
<213> ORGANISM: Artificial
<220> FEATURE:
<223> OTHER INFORMATION: Clone 4 thrombin binding sequence

<400> SEQUENCE: 5
ugcggauaac aagauagcaa agacu                                             25

<210> SEQ ID NO 6
<211> LENGTH: 25
<212> TYPE: RNA
<213> ORGANISM: Artificial
<220> FEATURE:
<223> OTHER INFORMATION: Clone 5 thrombin binding sequence

<400> SEQUENCE: 6
cuaccguaag agaacgagca gacuc                                             25

<210> SEQ ID NO 7
<211> LENGTH: 25
<212> TYPE: RNA
<213> ORGANISM: Artificial
<220> FEATURE:
<223> OTHER INFORMATION: Clone 6 thrombin binding sequence

<400> SEQUENCE: 7
```

-continued cgggacacua aggaacauaa aaguu                                              25

<210> SEQ ID NO 8
<211> LENGTH: 25
<212> TYPE: RNA
<213> ORGANISM: Artificial
<220> FEATURE:
<223> OTHER INFORMATION: Clone 7 thrombin binding sequence

<400> SEQUENCE: 8
ccgaagcucg gagaagcaca gaagc                                              25

<210> SEQ ID NO 9
<211> LENGTH: 25
<212> TYPE: RNA
<213> ORGANISM: Artificial
<220> FEATURE:
<223> OTHER INFORMATION: Clone 8 thrombin binding sequence

<400> SEQUENCE: 9
gggauugcac aagauagcgu agacu                                              25

<210> SEQ ID NO 10
<211> LENGTH: 25
<212> TYPE: RNA
<213> ORGANISM: Artificial
<220> FEATURE:
<223> OTHER INFORMATION: Clone 9 thrombin binding sequence

<400> SEQUENCE: 10
ggguguucac aagauagagu agacu                                              25

<210> SEQ ID NO 11
<211> LENGTH: 25
<212> TYPE: RNA
<213> ORGANISM: Artificial
<220> FEATURE:
<223> OTHER INFORMATION: Clone 10 thrombin binding sequence

<400> SEQUENCE: 11
gcuuugacac aagauacaau auagu                                              25

<210> SEQ ID NO 12
<211> LENGTH: 87
<212> TYPE: DNA
<213> ORGANISM: Artificial
<220> FEATURE:
<223> OTHER INFORMATION: Random Library Sequence
<220> FEATURE:
<221> NAME/KEY: misc_feature
<222> LOCATION: (19)..(43)
<223> OTHER INFORMATION: Where N at positions 19-43 can be A, T, C or G

<400> SEQUENCE: 12
ccgggctttg tgtcacttnn nnnnnnnnnn nnnnnnnnnn nnngctcgtt ctccttccct        60
ctcctatagt gagtcgtatt acagttg                                            87

<210> SEQ ID NO 13
<211> LENGTH: 87
<212> TYPE: DNA
<213> ORGANISM: Artificial
<220> FEATURE:
<223> OTHER INFORMATION: NheI Library

<400> SEQUENCE: 13
ccgggctttg tgtcacttta cgttcttatg ttctcactcg ctagctcgtt ctccttccct        60

```
ctcctatagt gagtcgtatt acagttg                                        87

<210> SEQ ID NO 14
<211> LENGTH: 28
<212> TYPE: DNA
<213> ORGANISM: Artificial
<220> FEATURE:
<223> OTHER INFORMATION: Biotinylated T7 Forward Primer
<220> FEATURE:
<221> NAME/KEY: misc_feature
<222> LOCATION: (1)..(1)
<223> OTHER INFORMATION: Where C at position 1 is Biotinylated

<400> SEQUENCE: 14
caactgtaat acgactcact ataggaga                                       28

<210> SEQ ID NO 15
<211> LENGTH: 19
<212> TYPE: DNA
<213> ORGANISM: Artificial
<220> FEATURE:
<223> OTHER INFORMATION: IsodC Reverse Primer
<220> FEATURE:
<221> NAME/KEY: misc_feature
<222> LOCATION: (1)..(1)
<223> OTHER INFORMATION: Where N is IsodC

<400> SEQUENCE: 15
nccgggcttt gtgtcactt                                                 19

<210> SEQ ID NO 16
<211> LENGTH: 82
<212> TYPE: DNA
<213> ORGANISM: Artificial
<220> FEATURE:
<223> OTHER INFORMATION: Capture Strand Rigidifying Oligonucleotide

<400> SEQUENCE: 16
gcttgttcgt tgtgtggggc actcatgtct aaatcgtttg tctatgcttg cgtcatttct    60
gggtatactg gtctgtggtg aa                                             82

<210> SEQ ID NO 17
<211> LENGTH: 15
<212> TYPE: DNA
<213> ORGANISM: Artificial
<220> FEATURE:
<223> OTHER INFORMATION: NheI Selection Oligonucleotide
<220> FEATURE:
<221> NAME/KEY: misc_feature
<222> LOCATION: (1)..(1)
<223> OTHER INFORMATION: Where the T at position 1 is Biotinylated

<400> SEQUENCE: 17
tgttctcact cgcta                                                     15

<210> SEQ ID NO 18
<211> LENGTH: 28
<212> TYPE: DNA
<213> ORGANISM: Artificial
<220> FEATURE:
<223> OTHER INFORMATION: T7 Forward Primer

<400> SEQUENCE: 18
caactgtaat acgactcact ataggaga                                       28

<210> SEQ ID NO 19
```

```
<211> LENGTH: 18
<212> TYPE: DNA
<213> ORGANISM: Artificial
<220> FEATURE:
<223> OTHER INFORMATION: Reverse Primer

<400> SEQUENCE: 19
ccgggctttg tgtcactt                                                       18

<210> SEQ ID NO 20
<211> LENGTH: 64
<212> TYPE: RNA
<213> ORGANISM: Artificial
<220> FEATURE:
<223> OTHER INFORMATION: Full length clone 1 aptamer

<400> SEQUENCE: 20
ggagagagaa ggagaacgag cuguuacuca caaaauagcg aagacuaagu gacacaaagc         60
ccgg                                                                      64

<210> SEQ ID NO 21
<211> LENGTH: 64
<212> TYPE: RNA
<213> ORGANISM: Artificial
<220> FEATURE:
<223> OTHER INFORMATION: Full length clone 2 aptamer

<400> SEQUENCE: 21
ggagagguaa guagaacgag cccggcguca caagauagac aaaacuaagu gacacaaagc         60
ccgg                                                                      64

<210> SEQ ID NO 22
<211> LENGTH: 64
<212> TYPE: RNA
<213> ORGANISM: Artificial
<220> FEATURE:
<223> OTHER INFORMATION: Full length clone 3 aptamer

<400> SEQUENCE: 22
ggagagggaa ggagaacgaa ccgggacuca caagauagac aauacuaagu gacacaaagc         60
ccgg                                                                      64

<210> SEQ ID NO 23
<211> LENGTH: 63
<212> TYPE: RNA
<213> ORGANISM: Artificial
<220> FEATURE:
<223> OTHER INFORMATION: Full length clone 4 aptamer

<400> SEQUENCE: 23
ggagagggaa ggagaacggc ugcggauaac aagauagcaa agacuaagug acacaaagcc         60
cgg                                                                       63

<210> SEQ ID NO 24
<211> LENGTH: 63
<212> TYPE: RNA
<213> ORGANISM: Artificial
<220> FEATURE:
<223> OTHER INFORMATION: Full length clone 5 aptamer

<400> SEQUENCE: 24
ggagagguag gagaacgagc cuaccguaag agaacgagca gacucaagug acacaaagcc         60
cgg                                                                       63
```

<210> SEQ ID NO 25
<211> LENGTH: 64
<212> TYPE: RNA
<213> ORGANISM: Artificial
<220> FEATURE:
<223> OTHER INFORMATION: Full length clone 6 aptamer

<400> SEQUENCE: 25
ggagagggaa ggagaacgag ccgggacacu aaggaacaua aaaguuaagu gacacaaagc    60
ccgg                                                                64

<210> SEQ ID NO 26
<211> LENGTH: 64
<212> TYPE: RNA
<213> ORGANISM: Artificial
<220> FEATURE:
<223> OTHER INFORMATION: Full length clone 7 aptamer

<400> SEQUENCE: 26
ggagagggaa ugauaacgag cccgaagcuc ggagaagcac agaagcaagu gacacaaagc    60
ccgg                                                                64

<210> SEQ ID NO 27
<211> LENGTH: 63
<212> TYPE: RNA
<213> ORGANISM: Artificial
<220> FEATURE:
<223> OTHER INFORMATION: Full length clone 8 aptamer

<400> SEQUENCE: 27
ggagagcgaa gagaacgagc gggauugcac aagauagcgu agacuaagug acacaaagcc    60
cgg                                                                 63

<210> SEQ ID NO 28
<211> LENGTH: 64
<212> TYPE: RNA
<213> ORGANISM: Artificial
<220> FEATURE:
<223> OTHER INFORMATION: Full length clone 9 aptamer

<400> SEQUENCE: 28
ggagagggaa agagaacgag cgggucuuca caagauagag uagacuaagu gacacaaagc    60
ccgg                                                                64

<210> SEQ ID NO 29
<211> LENGTH: 64
<212> TYPE: RNA
<213> ORGANISM: Artificial
<220> FEATURE:
<223> OTHER INFORMATION: Full length clone 10 aptamer

<400> SEQUENCE: 29
ggagacggaa ggauaacgag cgcuuugaca caagauacaa uauaguaagu gacaccaagc    60
ccgg                                                                64

<210> SEQ ID NO 30
<211> LENGTH: 25
<212> TYPE: RNA
<213> ORGANISM: Artificial
<220> FEATURE:
<223> OTHER INFORMATION: Toggle 25 aptamer

<400> SEQUENCE: 30
gggaacaaag cugaaguacu uaccc    25

<210> SEQ ID NO 31
<211> LENGTH: 124
<212> TYPE: DNA
<213> ORGANISM: Artificial
<220> FEATURE:
<223> OTHER INFORMATION: Portion of Capture Strand located 5' to linker,
      for non-fluorinated library

<400> SEQUENCE: 31
gctcgttctc cttccctctc cttttttttt tcaacaccac agaccagtat acccagaaat    60
gacgcaagca tagacaaacg atttagacat gagtgcccca cacaacgaac aagctttttt    120
ttta    124

<210> SEQ ID NO 32
<211> LENGTH: 28
<212> TYPE: DNA
<213> ORGANISM: Artificial
<220> FEATURE:
<223> OTHER INFORMATION: Portion of Capture Strand located 3' to linker,
      for non-fluorinated library

<400> SEQUENCE: 32
caactgtaat acgactcact ataggaga    28

<210> SEQ ID NO 33
<211> LENGTH: 96
<212> TYPE: DNA
<213> ORGANISM: Artificial
<220> FEATURE:
<223> OTHER INFORMATION: Random Library Sequence for incorporation of
      modified RNA
<220> FEATURE:
<221> NAME/KEY: misc_feature
<222> LOCATION: (19)..(43)
<223> OTHER INFORMATION: n is a, c, g, or t

<400> SEQUENCE: 33
ccgggctttg tgtcgcttnn nnnnnnnnn nnnnnnnnnn nnncttcctc tccctctccc    60
ttcctcttcc tcctatagtg agtcgtatta cagttg    96

<210> SEQ ID NO 34
<211> LENGTH: 124
<212> TYPE: DNA
<213> ORGANISM: Artificial
<220> FEATURE:
<223> OTHER INFORMATION: Portion of Capture Strand located 5' to linker,
      for fluorinated library

<400> SEQUENCE: 34
cctctcccTT cctcttcctc cttttttttt tcaacaccac agaccagtat acccagaaat    60
gacgcaagca tagacaaacg atttagacat gagtgcccca cacaacgaac aagctttttt    120
ttta    124

<210> SEQ ID NO 35
<211> LENGTH: 28
<212> TYPE: DNA
<213> ORGANISM: Artificial
<220> FEATURE:
<223> OTHER INFORMATION: Portion of Capture Strand located 3' to linker,
      for fluorinated library

```
<400> SEQUENCE: 35
caactgtaat acgactcact ataggagg                                          28

<210> SEQ ID NO 36
<211> LENGTH: 32
<212> TYPE: RNA
<213> ORGANISM: Artificial Sequence
<220> FEATURE:
<223> OTHER INFORMATION: Truncation of Clone 9

<400> SEQUENCE: 36
guguucacaa gauagaguag acuaagugac ac                                     32
```

DNA DISPLAY OF FOLDED RNA LIBRARIES ENABLING RNA-SELEX WITHOUT REVERSE TRANSCRIPTION

This application is a national stage application under 35 U.S.C. § 371 of PCT Application No. PCT/US2018/018634, filed Feb. 19, 2018, which claims the benefit of U.S. Provisional Patent Application Ser. No. 62/460,365, filed Feb. 17, 2017, which is hereby incorporated by reference in its entirety.

This invention was made with government support under AI 090745 awarded by the National Institutes of Health. The government has certain rights in the invention.

FIELD OF THE INVENTION

This invention is directed to a method of selecting an RNA molecule that binds to a target molecule, including the selection of RNA molecules bearing one or more modifications such as modified bases and modified ribosyl-phosphate groups.

BACKGROUND OF THE INVENTION

First characterized in 1990 independently by the laboratories of Szostak and Gold, oligonucleotide aptamers are DNA or RNA with high affinity for proteins or small molecules (Ellington et al., *Nature*, 346:818-822 (1990); Tuerk et al., *Science*, 249: 505-510 (1990); Gold et al., *Cold Spring Harbor Perspect. Biol.*, 4 (2012); Stoltenburg et al., *Biomol. Eng.*, 24:381-403 (2007)). Exhibiting advantages such as affinities comparable to those of antibodies, simplicity of synthesis, and general lack of immunogenicity, aptamers have found a place in the pharmaceutical market. The first aptamer drug approved by the FDA, Pegaptanib, targets age-related macular degeneration by binding to vascular endothelial growth factor (VEGF) (Kanwar et al., *Curr. Med. Chem.*, 22:2539-2557 (2015); Keefe et al., *Nat. Rev. Drug Discovery*, 9:537-550 (2010); Sundaram et al., *Eur. J. Pharm. Sci.*, 48:259-271 (2013); Sun et al., *Mol. Ther.— Nucleic Acids*, 3:e182 (2014); Santosh et al., *BioMed Res. Int.*, 2014:540451 (2014); Rudman, et al., *J. Biol. Chem.*, 273:20556-20567 (1998)). Several other aptamers are in late-stage clinical trials, and an unknown number are in laboratory development (Kanwar et al., *Curr. Med. Chem.*, 22:2539-2557 (2015); Keefe et al., *Nat. Rev. Drug Discovery*, 9:537-550 (2010); Sundaram et al., *Eur. J. Pharm. Sci.*, 48:259-271 (2013); Sun et al., *Mol. Ther.— Nucleic Acids*, 3:e182 (2014); Santosh et al., *BioMed Res. Int.*, 2014: 540451 (2014)). Aptamers are typically discovered using standard molecular biology techniques through an in vitro selection process termed SELEX (Systematic Evolution of Ligands by EXponential enrichment) (Stoltenburg et al., *Biomol. Eng.*, 24:381-403 (2007)). DNA libraries with random regions flanked by constant regions are synthesized using standard phosphoramidite chemistry and can be used directly in the selection of DNA aptamers. RNA libraries are generated by transcription of a T7 promoter-containing random DNA library using T7 RNA polymerase. Libraries are mixed with a target small molecule or protein and the bound fraction is recovered using a variety of isolation techniques. The recovered library is amplified with the polymerase chain reaction (PCR) for DNA aptamers or reverse transcription-PCR for RNA aptamers, the single-stranded DNA or RNA is regenerated from the PCR product and the selection cycle is repeated until the library is sufficiently enriched with target-binding aptamers.

Limitations to standard aptamer libraries (nuclease sensitivity, limited chemical diversity) have been overcome by the use of non-natural nucleotide analogs (Gold, et al., *PLoS One*, 5:e15004 (2010); Gupta et al., *J. Biol. Chem.*, 289: 8706-8719. (2014); Keefe et al., *Curr. Opin. Chem. Biol.*, 12:448-456 (2008); Lapa et al., *Mol. Biotechnol.*, 58:79-92 (2016); Ohsawa et al., *Anal. Sci.*, 24:167-172 (2008); Shoji et al., *J. Am. Chem. Soc.*, 129:1456-1464 (2007); Wang et al., *Curr. Med. Chem.*, 18:4126-4138 (2011)). For instance, the incorporation of 2'-fluoro pyrimidines into RNA by T7 RNA polymerase variants results in significant serum nuclease resistance, a major requirement for drug development. To improve chemical diversity, base-modified DNA aptamers have been readily utilized, largely owing to the discovery that family B DNA polymerases (including Vent, KOD, and Pfu) can accommodate C5-substituted thymidine base analogs (Gold et al., *Cold Spring Harbor Perspect. Biol.*, 4 (2012); Gold, et al., *PLoS One*, 5:e15004 (2010); Gupta et al., *J Biol. Chem.*, 289:8706-8719. (2014); Keefe et al., *Curr. Opin. Chem. Biol.*, 12:448-456 (2008); Lapa et al., *Mol. Biotechnol.*, 58:79-92 (2016); Ohsawa et al., *Anal. Sci.*, 24:167-172 (2008); Kuwahara et al., *Nucleic Acids Symp. Ser.*, 81-82 (2005); Kuwahara et al., *Molecules*, 15:5423-5444 (2010); Rohloff et al., *Mol. Ther. Nucleic Acids*, 3:e201 (2014); M. Kuwahara, et al., *Nucleic Acids Res.*, 34:5383-5394 (2006); M. Kuwahara, et al., *Molecules*, 15:8229 (2010)). In particular, SOMAmer technology, which incorporates short hydrophobic groups at the C5 position of uridine, improved the success rate of obtaining high-affinity aptamers from 30% to 80% for hundreds of targets (Rohloff et al., *Mol. Ther.—Nucleic Acids*, 3:e201 (2014)). Recently, the inventors reported a method termed SELection of Modified Aptamers, or SELMA, allowing for the incorporation of large modifications into DNA libraries, which was successfully used to obtain multivalent glycoclusters that mimic a conserved epitope on the HIV envelope protein gp120 (MacPherson et al., *Angew. Chem., Int. Ed.*, 50:11238-11242 (2011); Temme et al., *Chemistry*, 19:17291-17295 (2013); Temme et al., *Curr. Protoc. Chem. Biol.*, 7:73-92 (2015); Temme et al, *J. Am. Chem. Soc.*, 136:1726-1729 (2014)).

However, compared to DNA, successes with base-modified RNA aptamer libraries have not been as wide-spread, despite the superior serum nuclease resistance of 2'-F-modified RNA and greater folding space sampling of RNA libraries. An obstacle to development of base-modified RNA-SELEX is that it would require that two different types of enzymes (RNA polymerase and reverse transcriptase) tolerate the modified bases. It would be desirable, therefore, to develop a modified SELEX procedure that facilitates the selection of RNA aptamers that may contain modified RNA analogues.

The present invention is directed to overcoming these and other deficiencies in the art.

SUMMARY OF THE INVENTION

A first aspect of the invention relates to a method for selecting an RNA molecule that binds to a target molecule. This method includes: providing a pool of oligonucleotide complexes that each comprise a ds-DNA molecule and an RNA molecule, the ds-DNA molecule comprising a first DNA strand at least partially annealed to a first region of the RNA molecule, whereby a second region of the RNA molecule is free to adopt a secondary structure; exposing the pool to a target molecule and allowing the second region of the RNA to bind the target molecule; and selecting from the pool one or more oligonucleotide complexes comprising an RNA molecule having the second region bound to the target molecule.

In accordance with one particular embodiment, the first DNA strand comprises a 5' capture region that is unpaired within the ds-DNA molecule and the RNA molecule comprises the first region at the 5' end thereof and the second region extending from the first region to the 3' end thereof, wherein the first region of the RNA molecule is complementary to and annealed to the 5' capture region of the first DNA strand.

A second aspect of the invention relates to a kit for carrying out the method of the described invention. The kit includes: a ds-DNA optionally comprising a non-natural nucleic acid molecule at a 5' end of a template strand; a DNA capture strand that anneals to the template strand and comprises a first portion primer sequence tethered via a linker molecule to a second portion that includes a 5' capture region; and a DNA rigidifier strand that is capable of annealing to the second portion of the DNA capture strand; optionally including one or more of a DNA polymerase, dNTPs, an RNA polymerase, rNTPs of modified rNTPs, one or more buffer solutions.

The accompanying Examples demonstrate the successful generation and selection of RNA libraries in which the folded RNA is physically attached to the dsDNA that encodes it. The concept of displaying a difficult-to-amplify oligonucleotide on analogous dsDNA was introduced by Szostak and coworkers (Ichida et al., *J. Am. Chem. Soc.*, 127:2802-2803 (2005), which is hereby incorporated by reference in its entirety), and has been put into practice by several groups (MacPherson et al., *Angew. Chem., Int. Ed.*, 50:11238-11242 (2011); Yu et al., *Nat. Chem.*, 4:183-187 (2012); Renders et al., *Chem. Commun.*, 51:1360-1362 (2015), each of which is hereby incorporated by reference in its entirety). However, none of the prior work demonstrates the selection of tethered RNA library members while displayed on the encoding dsDNA, which can circumvent the need for reverse-transcription in the amplification of RNA libraries and therefore can be applied to RNA containing base modifications for which reverse transcription is inefficient. To promote RNA display on the dsDNA, the DNA library members are modified with a modified base, e.g., isodC, that is suitable to stall T7 polymerase and a 5' "capture strand" is provided to anneal to the nascent RNA transcript. This method was validated in a selection of RNA aptamers against human α-thrombin with dissociation constants in the low nanomolar range. This method will be useful in the discovery of RNA aptamers and ribozymes, and particularly those containing base modifications that make them resistant to accurate reverse transcription. For example, this method can be used with RNA containing alkyne-modified RNA analogues and post-transcriptional click modification in an RNA-version of SELMA (MacPherson et al., *Angew. Chem., Int. Ed.*, 50:11238-11242 (2011); Temme et al., *Chemistry*, 19:17291-17295 (2013); Temme et al., *Curr. Protoc. Chem. Biol.*, 7:73-92 (2015); Temme et al, *J. Am. Chem. Soc.*, 136:1726-1729 (2014), each of which is hereby incorporated by reference in its entirety).

BRIEF DESCRIPTION OF THE DRAWINGS

FIG. 2A is an illustration of Mfold-predicted secondary structure of Clone 9 (SEQ ID NO: 28). Mfold is available from Dr. Michael Zuker, The RNA Institute, SUNY at Albany (see Zuker, M., *Nucleic Acids Res.*, 31:3406-3415 (2003), which is hereby incorporated by reference in its entirety). FIG. 2B is an illustration of Mfold predicted secondary structure of the truncated Clone 9 (SEQ ID NO: 36, corresponding to nts 24-55 of SEQ ID NO: 28). FIG. 2C is a graph of the filter binding data of Clone 9 and the truncated form used in BLI. FIG. 2D is a graph of the BLI experimental and curve fit data.

FIG. 3A gel conditions: 10% acrylamide, 29:1 acrylamide:bis-acrylamide, stained with ethidium bromide. FIG. 3BA gel conditions: 8 M urea, 12.5% acrylamide, 29:1 acrylamide:bis-acrylamide, stained with Sybr Gold. Lanes 1-9 contain the same samples in both gels.

DETAILED DESCRIPTION OF THE INVENTION

As noted above, the present invention relates to a novel method for screening and selecting RNA aptamers, including RNA aptamers that may contain modified RNA analogues.

Nucleic acid aptamers are characterized by a single-strand and have secondary structure that may possess one or more stems (i.e., base-paired regions) as well as one or more non base-paired regions along the length of the stem. These non-base-paired regions can be in the form of a bulge or loop (e.g., internal loop) along the length of the stem(s) and/or a loop at the end of the one or more stem(s) (e.g., hairpin loop). These nucleic acid aptamers possess specificity in binding to a particular target molecule, and they non-covalently bind their target molecule through an interaction such as an ion-ion force, dipole-dipole force, hydrogen bond, van der Waals force, electrostatic interaction, stacking interaction or any combination of these interactions. Aptamers that bind to their target with low nM affinity, or sub-nM affinity, are particularly desirable, and aptamers that possess modified RNA to promote, e.g., stability and resistance to degradation, are also desirable.

Identifying suitable nucleic acid aptamers typically involves selecting aptamers that bind a particular target molecule with sufficiently high affinity and specificity from a pool or library of nucleic acids containing a random region of varying or predetermined length. For example, identifying suitable nucleic acid aptamers of the present invention can be carried out using a modification of the established in vitro selection and amplification scheme known as SELEX. The SELEX scheme is described in detail in U.S. Pat. No. 5,270,163 to Gold et al.; Ellington and Szostak, *Nature* 346:818-822 (1990); and Tuerk and Gold, *Science* 249:505-510 (1990), each of which is hereby incorporated by reference in their entirety. An established template-primer system (Bartel et al., *Cell* 67:529-536 (1991), which is hereby incorporated by reference in its entirety) can be adapted to produce RNA molecules having a stretch of about 38-40 random bases sandwiched between 5' and 3' constant regions.

Thus, in a first aspect of the present invention, a method for selecting an RNA molecule that binds to a target molecule is described herein and illustrated in the accompanying Examples. This method includes providing a pool of oligonucleotide complexes that each includes a ds-DNA molecule and an RNA molecule, the ds-DNA molecule including a first DNA strand at least partially annealed to a first region of the RNA molecule, whereby a second region of the RNA molecule is free to adopt a secondary structure. This is followed by exposing the pool to a target molecule and allowing the second region of the RNA to bind the target molecule. Then, selecting from the pool, one or more oligonucleotide complexes that includes an RNA molecule having the second region bound to the target molecule.

Figure 1:
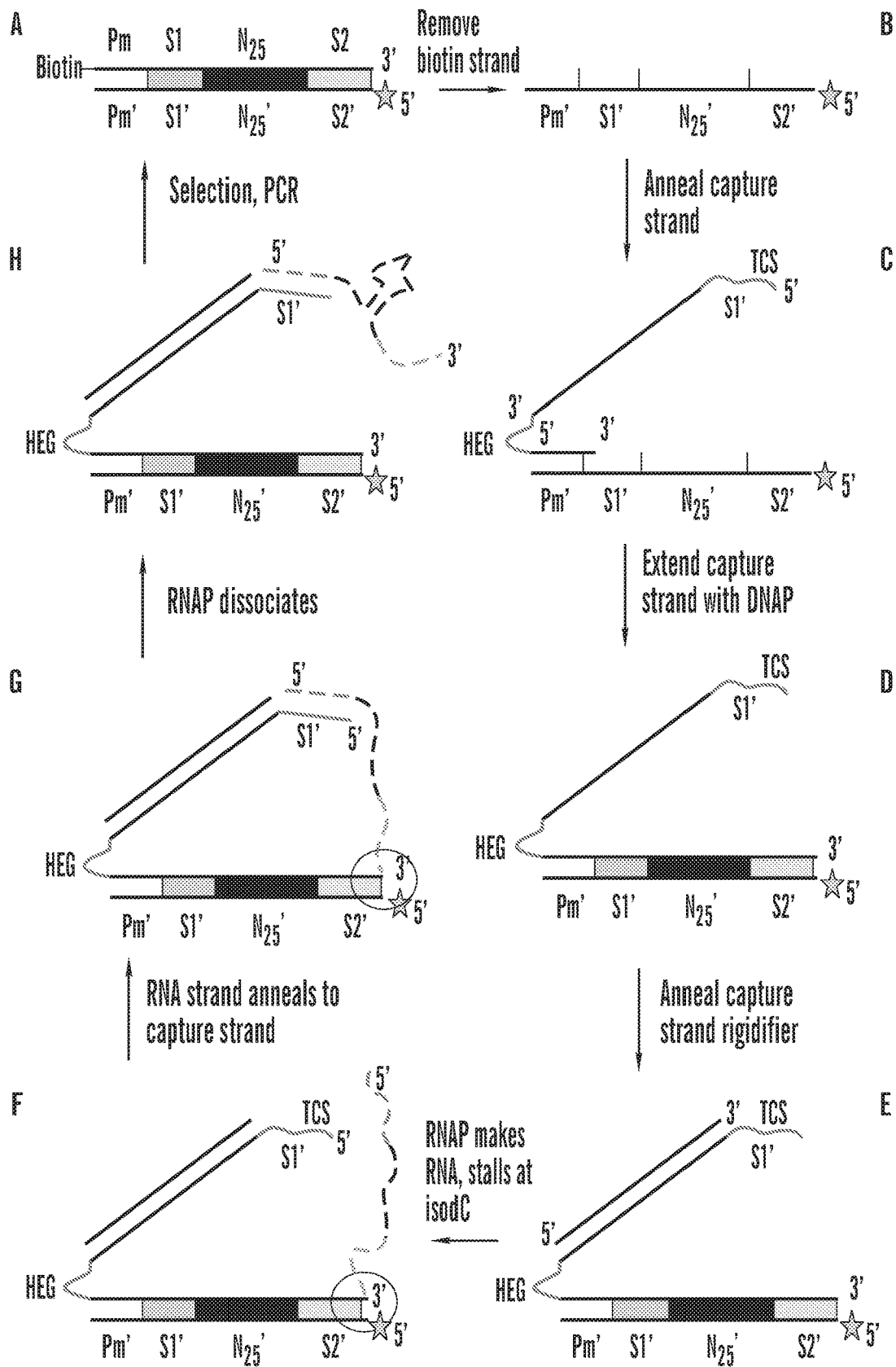
FIG. 1 is a schematic illustration of a process for the generation and selection of a DNA-displayed RNA library. Exemplary reagents, described below and referenced in FIG. 1, are considered non-limiting examples, and can be replaced with equivalent reagents. The black solid lines represent DNA; the dotted lines represent RNA; the grey line labeled HEG represents a hexaethyleneglycol spacer; the gray line labeled TCS represents the 5' terminal capture sequence complementary to S1; Pm represents the T7 promoter sequence; S1' represents the capture strand sequence; S2' represents the reverse primer; $N_{25}$ represents a random region; the star represents isodeoxycytidine; and the oval represents T7 polymerase. Step A shows the singly biotinylated, double stranded DNA. Step B shows the biotinylated strand removed using streptavidin magnetic beads. Step C shows the capture oligonucleotide annealed to the non-coding strand. Step D shows the regenerated the double stranded DNA with an 18 atom hexaethyleneglycol (HEG) spacer and 124-base single-stranded DNA (ssDNA) extension 5' of the coding strand. Step E shows an oligonucleotide annealed to the capture strand, rigidifying it while maintaining ssDNA at the 5' end. Step F shows the 5' end of the non-coding strand with its unnatural base, e.g., isodC, which causes T7 polymerase to stall (Tanasova et al., *ChemBioChem*, 16:1212-1218 (2015), which is hereby incorporated by reference in its entirety) at the end of the template. Step G shows the 5' ends of the capture strand and RNA transcript annealed "intrastructurally". Step H shows the dissociation of the T7 RNAP. Following selection and recovery of target-binding aptamers, the process can be repeated for multiple rounds.

This method for the selection and then regeneration of successive rounds of RNA libraries displayed on their encoded dsDNA is more fully described below with reference to FIG. 1. Briefly, the method involves designing a DNA library such that each DNA duplex can capture its corresponding RNA transcript on a "capture arm" (FIG. 1, Steps F-H).

Generation of this library starts with singly biotinylated, double stranded DNA (dsDNA) (FIG. 1, Step A), from which the coding strand is removed using streptavidin magnetic beads. The non-coding strand, as shown throughout FIG. 1, includes at its 5' terminus an unnatural base, e.g., isodC or isodG (star symbol in FIG. 1). A capture oligonucleotide is annealed to the non-coding strand (FIG. 1, Steps B, C) and extended using Bst 2.0 DNA polymerase (DNAP) to regenerate the dsDNA with a spacer molecule (e.g., 18 atom hexaethyleneglycol (HEG) spacer) that is attached to a single-stranded DNA (ssDNA) extension 5' of the coding strand (FIG. 1, Step D). In one embodiment, this ss-DNA is a 124-base sequence, although variations of this can be used. The 5' end of the capture strand contains a sequence (e.g., 5'-GCTCGTTCTCCTTCCCTCTCC-3', SEQ ID NO: 1, in the accompanying Examples) that complements the 5' end of the RNA strand encoded in the DNA library. An oligonucleotide is annealed to the capture strand at the region between the HEG spacer and the capture sequence, rigidifying it while maintaining ssDNA at the 5' end (FIG. 1, Step E). In one embodiment, where the ss-DNA is a 124-base sequence, the rigidifiying oligonucleotide is 82 nts in length. T7 RNA polymerase (RNAP), or its equivalent, and nucleotide triphosphates are then added to initiate transcription of the DNA library (FIG. 1, Step F). Presence of the unnatural base at the 5' end of the non-coding strand causes T7 polymerase to stall (Tanasova et al., *ChemBioChem*, 16:1212-1218 (2015), which is hereby incorporated by reference in its entirety) at the end of the template (FIG. 1, Step F). Stalling in this manner affords enough time for the 5' ends of the capture strand and RNA transcript to anneal "intrastructurally" (FIG. 1, Step G), thereby tethering the RNA strand to its encoding dsDNA. Once the T7 RNAP dissociates and the tethered RNA is allowed to adopt a secondary structure (with its 3' end free) (FIG. 1, Step H), the DNA/RNA library is amenable to selection. After selection, amplification of the selected library with a biotinylated forward primer and 5' isodC reverse primer regenerates the dsDNA library in its original form (FIG. 1, Step A), completing a single selection cycle. This cycle is intended to be repeated for multiple rounds of DNA/RNA library formation and selection.

It should be appreciated that during amplification of the ds-DNA library from the selected oligonucleotide complexes, a biotinylated forward primer is used and binds to a primer binding site near the 3' end of the template strand; and a reverse primer containing a terminal non-natural deoxynucleotide base (e.g., isodC or isodG) is used and binds to a primer binding site near the 3' end of the first portion of the first DNA strand. The amplified ds-DNA library is then recovered.

Based on the foregoing description, it should be apparent that in carrying out the process, the first DNA strand includes a first portion that is (or can be) annealed to a template strand, and a second portion that comprises the 5' capture region and is tethered at the 3' end thereof to the 5' end of the first portion via the linker molecule. The linker molecule is preferably a non-nucleotide linker such as hexaethyleneglycol, polyethylene glycol, an aliphatic hydrocarbon, or a peptide. The linker can also be a nucleotide spacer molecule comprising a plurality of mismatches at the 3' end of the template strand. It is important for the 5' capture region to remain unpaired within the ds-DNA molecule (i.e., free of secondary structure). The RNA molecule includes the first region at the 5' end thereof and the second region extending from the first region to the 3' end thereof, whereby the first region of the RNA molecule is complementary to and capable of annealing to the 5' capture region of the first DNA strand. See FIG. 1, Steps F-H.

While in the above description certain lengths of the oligonucleotides or regions thereof are identified. It should be appreciated by persons of skill in the art that the number of bases in an oligonucleotide or a region thereof, and the base composition thereof, can be adjusted to optimize the behavior of the molecules during the process described above. For instance, the length of the oligonucleotides should be adjusted such that the 5' ends of the capture strand and RNA transcript are physically close to one another while the RNA transcript remains tethered to the RNAP, thereby promoting the "intrastructural" annealling described above.

When designing the sequences of the capture arm of the DNA display construct, care was taken to minimize secondary structure formation. This was carried out using an iterative approach informed by the use of mFOLD prediction (Zuker, M., *Nucleic Acids Res.*, 31:3406-3415 (2003), which is hereby incorporated by reference in its entirety). In this manner, minimization of secondary structure allowed for annealing of the exemplary 82-base rigidifying oligonucleotide at low temperature (50° C.) despite its high predicted melting temperature ($T_m$~75° C. at 1 nM concentration). This is a desirable property for optimizing the process, because denaturation of the double stranded DNA library at higher temperatures will destroy the integrity of the library. The capture sequence itself, SEQ. ID NO: 1 in the provided Examples, was designed to have minimal secondary structure as well as a high $T_m$ with RNA. A key feature for high $T_m$ is the lack of A-U base pairs, which are known to destabilize RNA-DNA hybrids considerably (Martin et al., *Nucleic Acids Res.*, 8:2295-2299 (1980), which is hereby incorporated by reference in its entirety). As a result, a capture sequence was designed with $T_m$ of ~70° C. (at 1 nM concentration), a strong non-covalent linkage between the RNA and encoding DNA, capable of forming at the 37° C. transcription temperature. While a $T_m$ between the annealed 5' capture region and first region of the RNA molecule is preferably at least about 60° C., at least about 65° C., or at least about 70° C., sequences having lower $T_m$, such as, at least about 30° C., at least about 40° C., at least about 50° C., or at least about 55° C., can also be used. These lower melting temperatures are less preferred.

Unlike traditional SELEX where the RNA is typically supported on a solid support, i.e., as a partitioning device, the present invention involves retaining the RNA tethered to the ds-DNA containing the template. As such, there is no need to use reverse transcription to regenerate the template, because the selected RNA and its template remain tethered throughout each round of selection. In other words, each round of selection for RNA binding to its target necessarily involves selection of the tethered template DNA. This enhances the efficiency of SELEX by avoiding unnecessary steps. It also facilitates the introduction of modified RNA by the T7 polymerase or post-transcription modification. For example, in the SELMA process described above, click-chemistry can be used to introduce desired modification, e.g., glycosylation, onto modified nucleotides prior to selection but typically after FIG. 1, Step G (MacPherson et al., *Angew. Chem., Int. Ed.*, 50:11238-11242 (2011); Temme et al., *Chemistry*, 19:17291-17295 (2013); Temme et al., *Curr. Protoc. Chem. Biol.*, 7:73-92 (2015); Temme et al, *J. Am. Chem. Soc.*, 136:1726-1729 (2014), each of which is hereby incorporated by reference in its entirety).

As noted above, in certain embodiments the RNA molecule may have one or more modified nucleotides or modified ribosyl-phosphate groups. These modified nucleotides may be selected from the group of 2'-fluoro-ribonucleotides, 2'-amino-ribonucleotides, 2'-O-methyl-ribonucleotides, 5'-iodo-ribonucleotides, 5'-bromo-ribonucleotides, and alkyne-modified ribonucleotides. Furthermore the modified ribosyl-phosphate group may include a phosphorothioate-linked nucleotide.

As is well known in the art, different conditions can be used during amplification and selection to encourage the generation of high affinity aptamers. For example, optimization of aptamers can be achieved during (re)selection by using rigorous washing conditions in all steps, including the use of high temperature (37° C. or 45° C.) washing buffers, mild denaturants, and low salt and high salt washes, etc. The proposed stringent washing conditions are intended to select for aptamers that bind more tightly to the target molecules, and thereby improve the over affinity. An additional benefit of generating RNA aptamers that bind with higher affinity to the target is that lower concentrations of therapeutic agents of the present invention will be needed for therapeutic in vivo applications.

Another method to use for aptamer optimization is the use of a smaller bias during doping. For example, the library can be doped with a 2:1:1:1 ratio instead of 5:1:1:1. This will result in more library members being substantially different from the parent aptamer, allowing for more rapid evolution and selection of the highest affinity binders.

Modified versions of T7 polymerase can also be utilized. For example, a variety of selected T7 mutant polymerases have been identified which allow for efficient incorporation of 2'-O-methyl nucleotides and 2'-fluoro modified pyrimidines (see Meyer et al., *Nucl. Acids Res.* 43(15):7480-748 (2015), which is hereby incorporated by reference in its entirety).

In the procedure identified in FIG. 1, the rigidifying oligonucleotide serves to increase the likelihood that the RNA and capture strand will come into contact and anneal. Within the capture strand, the HEG spacer is used to maintain the ssDNA nature of the 5' capture sequence. Without this spacer, the 3' end of non-coding strand would be extended in steps C→D, creating a full-length complement of the capture arm that would block its ability to anneal to RNA. Any other suitable spacer molecule can be used as long as it is sufficient to block extension of the non-coding strand at its 3' end.

A further aspect of the present invention relates to one or more kits useful for carrying out the methods of the present invention. Each of the previously described components can be packaged into a kit, including one or more of the following: a ds-DNA optionally having a non-natural nucleic acid molecule at a 5' end of a template strand; a DNA capture strand that anneals to the template strand and has a first portion primer sequence tethered via a linker molecule to a second portion that includes a 5' capture region; a DNA rigidifier strand that is capable of annealing to the second portion of the DNA capture strand; and optionally one or more of a DNA polymerase, dNTPs, an RNA polymerase, rNTPs or modified rNTPs of the type described above, one or more buffer solutions, and instructions for carrying out the process described above and illustrated in FIG. 1. Quantities of the above reagents suitable for performing up to 5, 6, 7, 8, 9, or 10 or more rounds of selection and amplification can be provided.

Once high affinity RNA aptamers are identified, the secondary structure of each primary RNA aptamer can be predicted by computer programs such as MulFold or mFOLD (Jaeger et al., *Proc. Natl. Acad. Sci. USA* 86:7706-7710 (1989); Zuker, *Science* 244:48-52 (1989), each of which is hereby incorporated by reference in its entirety). Mutational studies can be conducted by preparing substitutions or deletions to map both binding sites on the RNA aptamer and its target molecule, as well as to further enhance aptamer binding affinity, as described in the accompanying Examples.

Aptamers generated from SELEX experiments can be optimized to produce second generation aptamers with improved properties (Eaton et al., "*Bioorg. Med. Chem.* 5:1087-1096 (1997), which is hereby incorporated by reference in its entirety). Through successive rounds of affinity maturation of a primary SELEX clone, it is possible to obtain aptamers that possess improved affinity for their target as compared to the original clone. Therefore, prior to using aptamers in cell-based experiments, each aptamer can be optimized using the following considerations:

Find the minimal aptamer sequence within the SELEX clone to identify the domain to subject to affinity maturation. This will lead to more desirable, smaller aptamers, which should be better for fusing with alternative functional domains and for in vivo delivery;

It is important to know if the aptamers are selective for their intended target molecule or if they bind indiscriminantly to structurally related, non-target molecules; and Additionally, forming targeted delivery vehicles includes fusing the aptamer sequence with one or more nucleic acid or non-nucleic acid based delivery molecules, optionally with one or more additional aptamers for the same target molecule. This will enhance internal delivery of the aptamers to cell targets of interest and decrease their off-rate from the target molecule of interest. The formation of these fusion molecules should be possible without impacting the aptamer ability to bind specifically to a particular target molecule of interest.

As used herein, "nucleic acid" includes both DNA and RNA, in both D and L enantiomeric forms, as well as derivatives thereof (including, but not limited to, 2'-fluoro-, 2'-amino, 2'O-methyl, 5'iodo-, and 5'-bromo-modified polynucleotides). Nucleic acids containing modified nucleotides (Kubik et al., *J Immunol.* 159:259-267 (1997); Pagratis et al., *Nat. Biotechnol.* 15:68-73 (1997), each which is hereby incorporated by reference in its entirety) and the L-nucleic acids (sometimes termed Spiegelmers®), enantiomeric to natural D-nucleic acids (Klussmann et al., *Nat. Biotechnol.* 14:1112-1115 (1996) and Williams et al., *Proc. Natl. Acad. Sci. USA* 94:11285-11290 (1997), each which is hereby incorporated by reference in its entirety), and non-natural bases are used to enhance biostability. In addition, the sugar-phosphate backbone can be replaced with a peptide backbone, forming a peptide nucleic acid (PNA), other natural or non-natural sugars can be used (e.g., 2'-deoxyribose sugars), or phosphothioate or phosphodithioate can be used instead of phosphodiester bonds.

Increasing the number of aptamer domains in a single molecule, i.e., a multivalent aptamer, also is shown to decrease the dissociation of the aptamer from its target. Therefore, the present invention also contemplates aptamer constructs that include a series of target molecule-binding aptamers that are joined together by linking nucleotides sequences that do not adversely affect the secondary structure of the individual aptamer domains. Multivalent aptamers of this type can be constructed as described in Shi et al., *Proc Natl Acad Sci USA* 96(18):10033-10038 (1999) (describing pentavalent aptamer constructs); Xu and Shi, *Nucl Acids Res* 37(9):1-9 (2009) (describing di-dimeric aptamer construct with three-way junction); U.S. Patent Application Publ. No. 20050282190 to Shi et al. (describing multimeric aptamer constructs containing three-way junctions), each of which is hereby incorporated by reference in its entirety. Before joining two functional RNA molecules, it is often beneficial to first predict the secondary structures of the chimeric nucleic acid molecule to ensure that their combination is unlikely to disrupt their secondary structures. Secondary structure predictions can be performed using a variety of software including, without limitation, RNA Structure Program (Dr. David Mathews, University of Rochester) and MFold (Dr. Michael Zuker, The RNA Institute, SUNY at Albany), among others. In certain embodiments, the aptamer domains can bind to the same binding site on the target molecule. In alternative embodiments, the aptamer domains can bind to more than one distinct site on the target molecule.

Sequences that stabilize the aptamer can also be introduced. One example of a stabilization sequence is an exonuclease-blocking sequence linked to an aptamer sequence. In particular, a stable tetra-loop near the 3' end of the aptamer can be engineered. Because of its highly stacked and relatively inaccessible structure, the UUCG tetra-loop (Cheong et al., *Nature* 346:680-682 (1990), which is hereby incorporated by reference in its entirety) can be used to stabilize nucleic acid molecules against degradation by 3' exonucleases and to serve as a nucleation site for folding (Varani, *Annu. Rev. Biophys. Biomol. Struct.* 24:379-404 (1995), which is hereby incorporated by reference in its entirety). Structurally, this type of loop is also used as a "U-turn" to close a stem region to make the strand continuous as a single molecular entity. Suitable U-turns for RNA include, without limitation, members of the UNCG and GNRA tetraloop families (Varani, *Annu. Rev. Biophys. Biomol. Struct.* 24:379-404 (1995), which is hereby incorporated by reference in its entirety). Suitable U-turns for DNA include, without limitation, members of the GNRA tetraloop family (Varani, "*Annu. Rev. Biophys. Biomol. Struct.* 24:379-404 (1995), which is hereby incorporated by reference in its entirety).

Another example of a stabilization sequence is an "S35 motif" which yields a virtually closed structure resistant to nucleolytic degradation. The S35 motif, constructed by creating complementary 5' and 3' ends, has been shown to cause an over 100-fold increase in accumulation of a tRNA-ribozyme chimerical transcript in stably transduced cell lines (Thompson et al., *Nucleic Acids Res.* 23:2259-2268 (1995), which is hereby incorporated by reference in its entirety). Its use with in vivo aptamer expression has been demonstrated previously. See Shi et al., *Mol Cell Biol* 17(5):2649-2657 (1997); U.S. Pat. No. 6,458,559 to Shi et al., each of which is hereby incorporated by reference in its entirety.

Having prepared and optimized the aptamer obtained in accordance with the present invention, the aptamers can be formulated as one component of a molecular delivery agent that also includes a cell targeting component that is covalently or non-covalently linked to the nucleic acid aptamer molecule. The cell targeting component can be another aptamer, an antibody or binding fragment thereof, or an antibody mimic that is specific for, e.g., a cell surface molecule that is present on the target cell type. According to this approach, the cell targeting component binds to a cell surface molecule on the target cell type, and the molecular delivery agent is taken up by the cell and the nucleic acid aptamer molecule is internalized into the cell where it can bind to and interact with the target molecule of interest to modify (typically inhibiting) its activity.

A further aspect of the invention relates to a pharmaceutical composition that includes a pharmaceutically acceptable carrier and an aptamer or molecular delivery agent of the present invention.

Pharmaceutical compositions suitable for injectable or parental use (e.g., intravenous, intra-arterial, intramuscular, etc.) or intranasal use may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable carriers and/or excipients, include, but are not limited to sterile liquids, such as water, saline solutions, and oils, with or without the addition of a surfactant and other pharmaceutically and physiologically acceptable carriers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

The pharmaceutical compositions can also include one or more additives or preservatives, or both.

Effective amounts of the aptamer or molecular delivery agent may vary depending upon many different factors, including mode of administration, target site, physiological state of the patient, other medications administered, and whether treatment is prophylactic or therapeutic. Treatment dosages need to be titrated to optimize safety and efficacy. The amount of aptamer or molecular delivery agent depends on the frequency of administration, the rate of clearance, and the patient population (e.g., adult or child). For example, dosages may vary from 1 µg-5 mg per dose and more usually from 5-1000 µg per dose for human administration.

By way of example, using thrombin as a target in carrying out the process illustrated in FIG. 1, various aptamers have been identified as shown in Table 1 below.

TABLE 1

Selected Thrombin Binding Sequences
(After Ten Rounds)

| Clone | SEQ ID NO | Sequence |
|---|---|---|
| 1 | 2 | UGUUACUCACAAAAUAGCGAAGACU |
| 2 | 3 | CCGGCGUCACAAGAUAGACAAAACU |

TABLE 1-continued

Selected Thrombin Binding Sequences
(After Ten Rounds)

| Clone | SEQ ID NO | Sequence |
|---|---|---|
| 3 | 4 | CGGGACUCACAAGAUAGACAAUACU |
| 4 | 5 | UGCGGAUAACAAGAUAGCAAAGACU |
| 5 | 6 | CUACCGUAAGAGAACGAGCAGACUC |
| 6 | 7 | CGGGACACUAAGGAACAUAAAAGUU |
| 7 | 8 | CCGAAGCUCGGAGAAGCACAGAAGC |
| 8 | 9 | GGGAUUGCACAAGAUAGCGUAGACU |
| 9 | 10 | GGGUGUUCACAAGAUAGAGUAGACU |
| 10 | 11 | GCUUUGACACAAGAUACAAUAUAGU |

In Table 1, only the random region is illustrated. The full length clones appear in Table 4 (see Example 6, infra). Of the clones shown in Table 1, the preferred clones are clones 2, 3, 8, and 9, each of which exhibits Kd values below 10 nM and Fbmax values exceeding 60. Clones 2 and 9 both displayed Fbmax values exceeding 70 nM, with clone 9 being preferred. See FIG. 2A, 2B.

EXAMPLES

The following Examples are presented to illustrate various aspects of the invention, but are not intended to limit the scope of the claimed invention.

Materials and Methods for Examples 1-7

Experimental Materials and Instruments

Synthetic DNA oligonucleotides were purchased from Integrated DNA Technologies. Vent(exo-) DNA polymerase, Bst 2.0 warm start DNA polymerase, T7 RNA polymerase, T4 polynucleotide kinase, hydrophilic streptavidin magnetic beads, dNTPs, rNTPs, NheI-HF, EcoRI and BSA was purchased from New England Biolabs. DNA grade Sephadex G-50 was purchased from GE healthcare. Biotinylated D-Phe-Pro-Arg-chloromethylketone (PPACK) covalent inhibitor-bound human α-thrombin was purchased from Haematologic Technologies. GelRed DNA stain was purchased from Biotium, and Sybr Gold nucleic acid gel stain was purchased from Life Technologies. TOPO-TA cloning kit was purchased from Life Technologies. Chemicals, electrophoresis reagents and equipment were purchased from VWR, Sigma and Bio-Rad. γ-AT$^{32}$P was purchased from Perkin Elmer. Table 2 contains the commercially purchased oligonucleotides.

TABLE 2

Oligonucleotides Used in Examples

| Name | Sequence | SEQ. ID NO |
|---|---|---|
| Random Library | CCGGGCTTTGTGTCACTTNNNNNNNNNNNNNNNNNNNNNNNNNG CTCGTTCTCCTTCCCTCTCCTATAGTGAGTCGTATTACAGTTG | 12 |
| NheI Library | CCGGGCTTTGTGTCACTTTACGTTCTTATGTTCTCACTCGCTAG CTCGTTCTCCTTCCCTCTCCTATAGTGAGTCGTATTACAGTTG | 13 |
| Biotinylated T7 For Primer | Biotin-CAACTGTAATACGACTCACTATAGGAGA | 14 |
| IsodC Rev Primer | isodC-CCGGGCTTTGTGTCACTT | 15 |
| Capture Strand (CS) | <u>GCTCGTTCTCCTTCCCTCTCC</u>TTTTTTTTTTCAACACCACAGAC CAGTATACCCAGAAATGACGCAAGCATAGAC<u>AAACGATTTAGAC ATGAGTGCCCCACACAACGAACAAG</u>CTTTTTTTTA-Z-CAACTGTAATACGACTCACTATAGGAGA | 31, 32 |
| CS Rigidifier | GCTTGTTCGTTGTGTGGGGCACTCATGTCTAAATCGTTTGTCTA TGCTTGCGTCATTTCTGGGTATACTGGTCTGTGGTGAA | 16 |
| NheI SelectiON 15mer | Biotin-TGTTCTCACTCGCTA | 17 |
| Unmodified T7 For Primer | CAACTGTAATACGACTCACTATAGGAGA | 18 |
| Unmodified Rev Primer | CCGGGCTTTGTGTCACTT | 19 |

In Table 2, all oligonucleotides are shown in 5'-3' orientation. For the random library (SEQ ID NO: 12), the random sequence was not biased. For the NheI library (SEQ ID NO: 13), the NheI site is underlined, and the selection oligonucleotide binding site is bold. For the capture strand (CS), the CS rigidifier binding site is underlined, the capture sequence is in bold and Z represents a hexaethyleneglycol spacer.

Example 1—Library Construction

A starting random double stranded DNA (dsDNA) library was produced by standard PCR of a synthetic random single stranded DNA (ssDNA) library using a biotinylated forward primer and isodC reverse primer using vent-exo DNA polymerase (refer to Table 2 for sequence information). A 200 µl PCR reaction consisted of 85 pmol biotinylated forward primer, 80 pmol isodC reverse primer, 5 pmol negative strand template, 1× thermopol buffer, 4 units Vent (exo-) DNA polymerase, 200 uM each dNTP and cycling at 95° C. for 60 seconds followed by 6 cycles of 95° C. for 30 seconds, 57° C. for 30 seconds, and 72° C. for 10 seconds. Following PCR amplification, the reaction was quenched by addition of 5 µl of 0.5 M EDTA and 25 µl of 4 M NaCl. To remove the biotinylated strand, the crude PCR product was incubated with 0.28 mg (70 µl) hydrophilic streptavidin magnetic beads for 30 minutes. The beads were washed twice with wash buffer (20 mM Tris pH 8, 500 mM NaCl) and then resuspended in 40 µl 0.1 M NaOH for 4 minutes followed by application of a magnetic separator and transfer of the supernatant to 4 µl 1 M HCl and 1 µl Tris pH 8. For generation of the positive control isodC ssDNA, the same primers were used to amplify a starting NheI positive control template in a PCR reaction and the product was treated in an identical manner with streptavidin magnetic beads to generate the 5' isodC ssDNA library.

For incorporation of the capture arm into the random library, 23 µl of the isolated single stranded DNA (above) was combined with 40 pmol capture strand and 5 ul 10× thermopol buffer in a volume of 48 µl. For inclusion of the NheI positive control sequence at 1:1000, 2.3 µl of a 1/100 dilution of the NheI positive control sequence was also added. The mix was heated to 95° C. for 60 sec and cooled to 57° C. The tube was placed on ice and 1 µl 10 mM dNTPs were added followed by the addition of 8 units Bst 2.0 warmstart DNA polymerase. The reaction was placed at 60° C. for 90 seconds and briefly cooled on ice before buffer exchange through a spin column loaded with DNA-grade Sephadex G50 equilibrated with 20 mM Tris pH 8, 4 mM MgSO$_4$.

To rigidify the capture arm with a complimentary 82mer oligonucleotide, 16 µl of the buffer-exchanged product was combined with 2 µl 10× RNA polymerase buffer and 1.3 µl rigidifying oligonucleotide (10 uM) and the mixture was incubated at 50° C. for 5 minutes. To remove unwanted biotinylated contaminants, the mixture was incubated with 0.08 mg hydrophilic streptavidin magnetic beads for 30 minutes and the supernatant retained. For transcription and RNA capture by its encoding DNA, the reaction was then cooled on ice and 0.2 µl DTT, 1 µl of 10 mM rNTPs and 5 units T7 RNA polymerase was added and the reaction was incubated at 37° C. for 8 minutes. In the NheI-based selection experiment, a negative control experiment was also performed in which the transcription step was omitted. The negative control sample was otherwise treated identically to the transcribed library.

Example 2—Control Selection with Spiked Library

The spiked NheI-containing sequence was selected by binding to a short complementary sequence. Briefly, the transcription reaction (or non-transcribed reaction in the negative control) was diluted into 50 µl with water and incubated with 50 nM of the biotinylated complementary 15mer for 10 minutes at 37° C. and then mixed with 0.1 mg hydrophilic streptavidin magnetic beads for 20 minutes. The supernatant was removed and the beads were resuspended in 30 µl elution buffer (20 mM Tris pH 8, 50 mM NaCl, 10% Tween-20, 150 ug/ml BSA) and placed in a 70° C. dry bath for 5 minutes, after which the supernatant was used in a PCR amplification reaction.

Example 3—Thrombin Selection

The RNA-displayed DNA library was selected for binding to biotinylated PPACK-bound human α-thrombin by incubation at varying thrombin concentrations and times, starting with 10 nM for 1 hour in round 1 and decreasing to 1 nM for 5 minutes in round 10 (Table 3). Thrombin-bound library was recovered by incubation with 0.1 mg streptavidin magnetic beads for 30 minutes, followed by washing with 100 µl and 150 µl selection buffer (20 mM Tris pH 8, 150 mM NaCl, 2 mM $MgSO_4$, 0.05% Tween-20). The beads were resuspended in 30 µl elution buffer and placed in a 95 degree dry bath for 3 minutes before removal with a magnetic rack, after which the supernatant was used in a PCR amplification reaction.

TABLE 3

Thrombin Aptamer Selection Conditions

| Round | [Thrombin] | Binding Time | # PCR Cycles for Recovery |
|---|---|---|---|
| 1 | 10 nM | 1 hour | 14 |
| 2 | 10 nM | 1 hour | 14 |
| 3 | 10 nM | 1 hour | 14 |
| 4 | 10 nM | 1 hour | 14 |
| 5 | 10 nM | 1 hour | 14 |
| 6 | 10 nM | 1 hour | 14 |
| 7 | 10 nM | 1 hour | 12 |
| 8 | 10 nM | 30 min | 10 |
| 9 | 10 nM | 5 min | 11 |
| 10 | 1 nM | 5 min | 14 |

Example 4—Amplification

For either type of selection step, the 30 µl eluted binders (above) were added to a 230 µl PCR reaction mix containing 35 pmol biotinylated forward primer, 35 pmol isodC reverse primer, 1× thermopol buffer, and 200 uM dNTPs. 30 µl of the 230 µl pre-mix was added to a single PCR tube, after which 0.6 units Vent(exo-) polymerase was added. The reaction was mixed, 10 µl amounts were distributed to two other tubes and all three tubes were amplified at the above described thermal cycling conditions (95° C. for 30 seconds, 57° C. for 30 seconds, 72° C. for 10 seconds) for varying cycle numbers, typically 10, 12 and 14 cycles. 5 µl from each tube was run on a 2% agarose DNA gel and the optimal cycle number was determined based on the appearance of 87 bp product. Then, 4 units of vent(exo-) polymerase was added to the remaining 200 µl of pre-mix and the reaction distributed over 4 tubes and amplified with the optimized cycle number, yielding double stranded DNA to be used in the next round of library generation and selection. Alternatively, for the NheI susceptibility studies, 4 µl of the PCR product was added directly to a restriction digest containing 1× Cutsmart buffer and 10 units of NheI HF in a total volume of 20 µl. 5 µl of the digestion product was run on a 6% non-denaturing polyacrylamide gel and stained with GelRed DNA stain.

Example 5—Cloning and Sequencing

The thrombin binding library recovered after round 10 was amplified using unmodified forward and reverse primers and the PCR product was cloned into plasmid pCR2.1 using a TOPO-TA kit. Ten *E. coli* colonies were grown overnight in liquid culture and the plasmids isolated using a Qiagen plasmid mini-prep kit and submitted for sequencing.

Example 6—RNA Preparation and Filter Binding Assay

Plasmids isolated above were digested with EcoRI restriction enzyme and used as template in a PCR reaction with T7 forward and isodC reverse primers, resulting in dsDNA template suitable for transcription. RNA from clones 1-10 was generated by transcription of the PCR products in 50 µl reactions, each containing 1× transcription buffer, 5 µl crude PCR product, 500 uM NTPs, and 15 units T7 RNA polymerase, incubated for 4 hours at 37° C. The RNA products were run on a 12% polyacrylamide gel and the 64-base band excised. The gel slices were crushed and soaked in 100 µl water at room temperature overnight, and supernatant was passed through a desalting column loaded with sephadex G-50 as a final cleanup step.

Figure 5A:
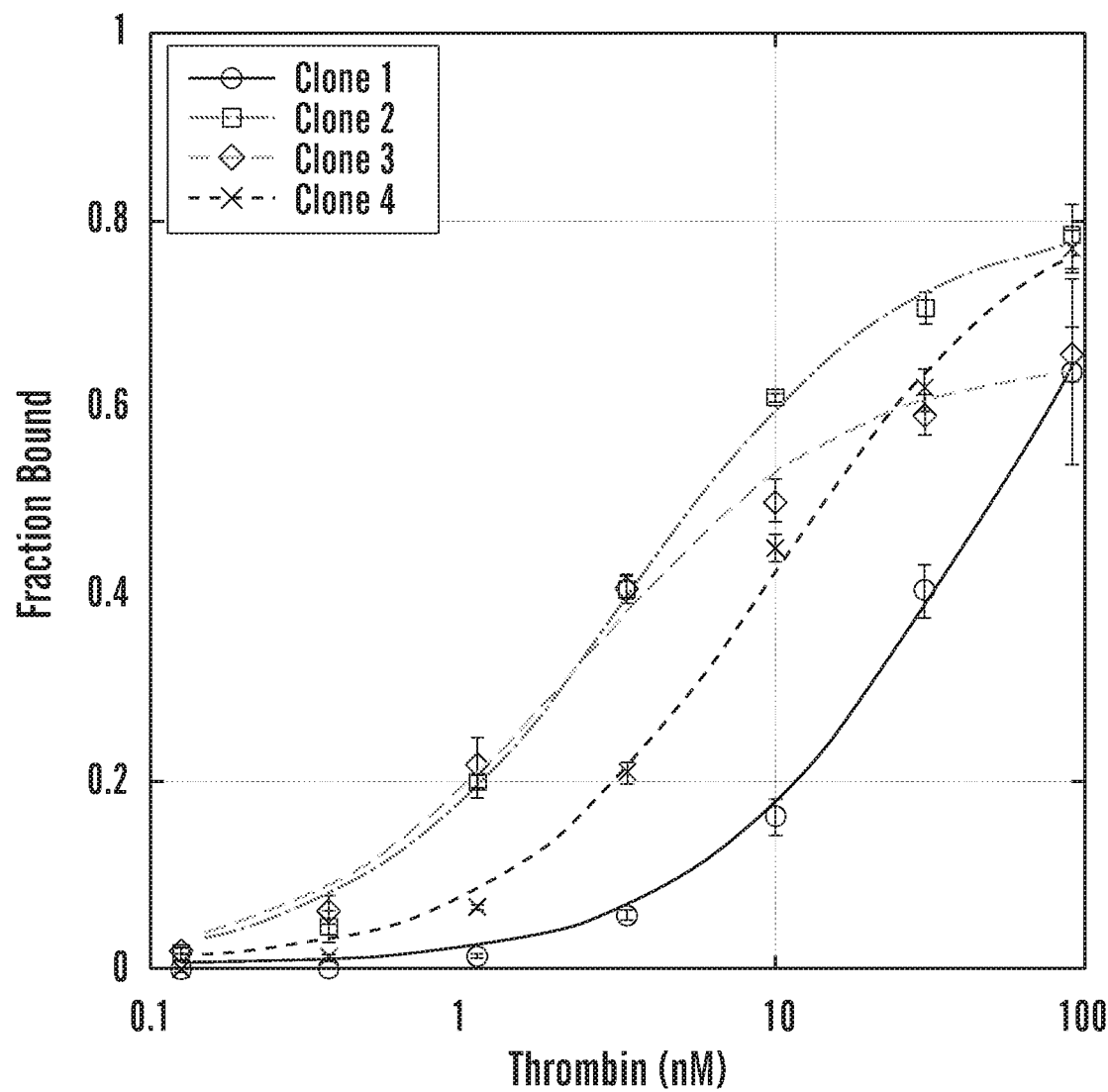
FIGS. 5A and 5B are graphs of filter binding curves from Example 6. Clone 1 (SEQ ID NO: 20), clone 2 (SEQ ID NO: 21), clone 3 (SEQ ID NO: 22), and clone 4 (SEQ ID NO: 23) are shown in FIG. 5A. Clone 6 (SEQ ID NO: 25), clone 8 (SEQ ID NO: 27), clone 9 (SEQ ID NO: 28), and clone 10 (SEQ ID NO: 29) are shown in FIG. 5B.
Figure 5B:
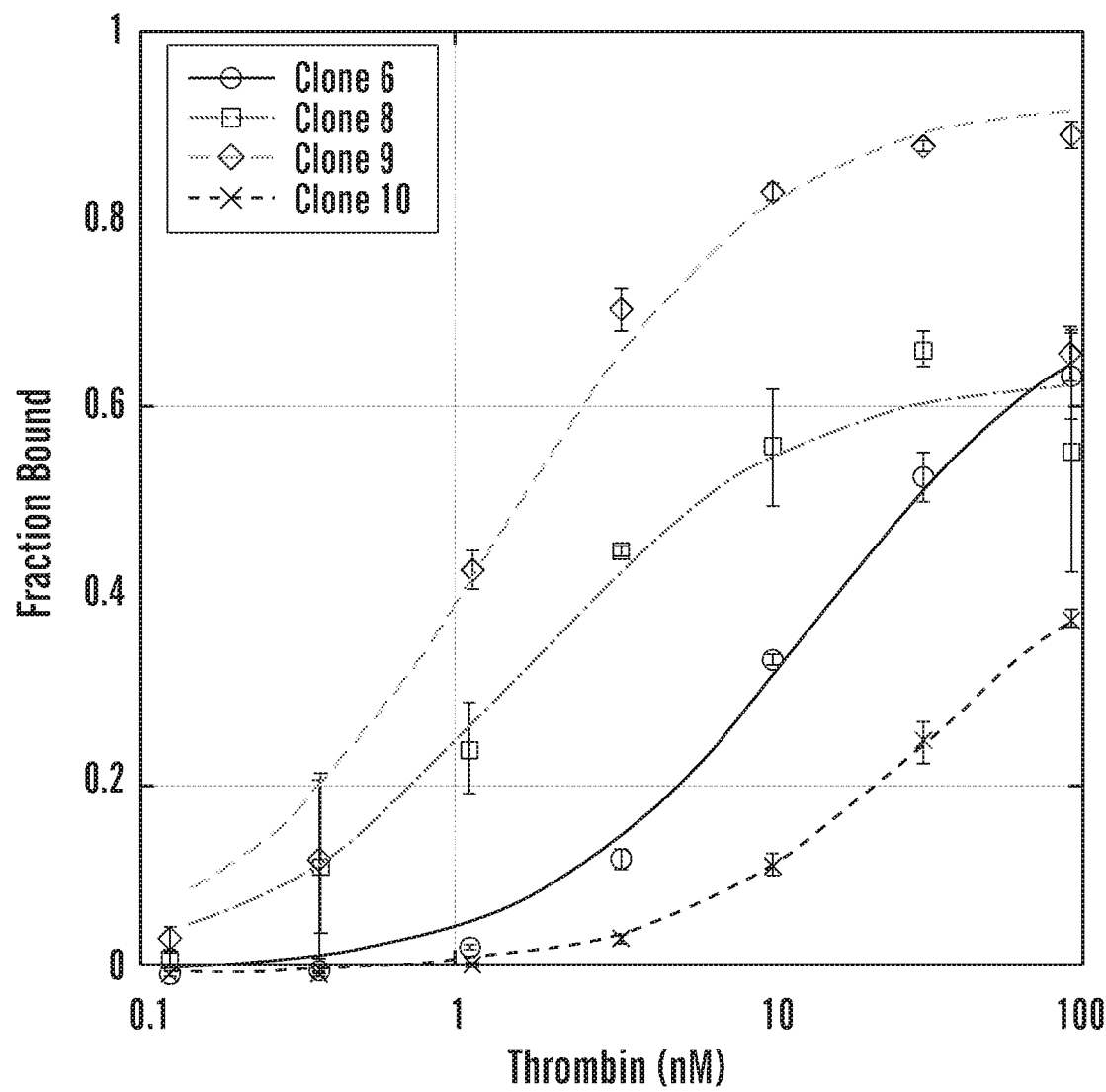

Binding buffer was prepared as 20 mM Tris pH 7.5, 150 mM NaCl, 2 mM $MgSO_4$, and 50 ug/mL BSA. RNA products were 5'-radiophosphoylated using T4 polynucleotide kinase, 200 nM $\gamma$-$AT^{32}P$ in 30 µl of 1× PNK buffer. After 30 minute at 37° C., the reactions were passed through a desalting column loaded with sephadex G-50 to remove salts and excess $\gamma$-$AT^{32}P$. 10-100 fmol of the 5'-$^{32}P$ labeled RNA was diluted into 50 µL of binding buffer and heated to 70° C. for 3 minutes, then cooled to RT to promote proper folding. Thrombin was serially diluted in binding buffer from 50 µM stock solution. For each clone studied, 50 µL aliquots of each thrombin dilution were pipetted into low retention 0.5 mL tubes (USA Scientific). 5 µl of the labeled and folded RNA was then added to each dilution and incubated at 22° C. for 30 minutes. Following incubation, the aliquots were passed through a 96 well sandwich filtration apparatus loaded with activated nitrocellulose/PVDF. Each well was then washed with 200 ul of freshly prepared binding buffer. The membranes were then dried under vacuum, wrapped in cellophane, and exposed to a phosphorimaging plate. The plate was imaged after an appropriate length of time for adequate exposure. The data (FIGS. 5A-5B) were then fit to $F_{bound}=(F_{max}[\text{Thrombin}])/(K_d+[\text{Thrombin}])$. The results are tabulated in Table 4.

TABLE 4

Full sequences and binding constants of oligonucleotides tested in filter binding assay

| Clone | SEQ ID NO | Sequence | $K_d$ (nM) | $Fb_{max}$ |
|---|---|---|---|---|
| 1 | 20 | GGAGAGAGAAGGAGAACGAGCUGUUACUCACAAAAUAGCGAAGACUAAGUGACACAAAGCCCGG | 44.7 ± 4.6 | 95.6 ± 4.4 |
| 2 | 21 | GGAGAGGUAAGUAGAACGAGCCCGGCGUCACAAGAUAGACAAAACUAAGUGACACAAAGCCCGG | 3.5 ± 0.3 | 80.6 ± 1.6 |
| 3 | 22 | GGAGAGGGAAGGAGAACGAACCGGGACUCACAAGAUAGACAAUACUAAGUGACACAAAGCCCGG | 2.4 ± 0.3 | 65.3 ± 1.9 |

TABLE 4-continued

Full sequences and binding constants of oligonucleotides tested in filter binding assay

| Clone | SEQ ID NO | Sequence | $K_d$ (nM) | $Fb_{max}$ |
|---|---|---|---|---|
| 4 | 23 | *GGAGAGGGAAGGAGAACGGC*UGCGGAUAACAAGAUAGCAAAGACUAAG*UGACACAAAGCCCGG* | 10.0 ± 0.9 | 84.5 ± 2.3 |
| 5 | 24 | *GGAGAGGUAGGAGAACGAGC*CUACCGUAAGAGAACGAGCAGACUC*AAGUGACACAAAGCCCGG* | NB | ND |
| 6 | 25 | *GGAGAGGGAAGGAGAACGAGC*CGGGACACUAAGGAACAUAAAAGUU*AAGUGACACAAAGCCCGG* | 13.8 ± 1.9 | 74.5 ± 3.2 |
| 7 | 26 | *GGAGAGGGAAUGAUAACGAGC*CCGAAGCUCGGAGAAGCACAGAAGC*AAGUGACACAAAGCCCGG* | NB | ND |
| 8 | 27 | *GGAGAGCGAAGAGAACGAGC*GGGAUUGCACAAGAUAGCGUAGAC*UAAGUGACACAAAGCCCGG* | 1.6 ± 0.4 | 63.5 ± 3.3 |
| 9 | 28 | *GGAGAGGGAAAGAGAACGAGC*GGGUGUUCACAAGAUAGAGUAGAC*UAAGUGACACAAAGCCCGG* | 1.4 ± 0.2 | 92.3 ± 3.1 |
| 10 | 29 | *GGAGACGGAAGGAUAACGAGC*GCUUUGACACAAGAUACAAUAUAGU*AAGUGACACCAAGCCCGG* | 36.4 ± 2.8 | 52.9 ± 1.7 |

In each sequence, the central region contains sequences derived from random sequence region, and the complement of capture sequence and complement of reverse primer are both italicized.
NB = no binding;
ND = not determined.
The complement of the capture sequence may contain slight mutations from the capture sequence complement present in the starting library, possibly accumulated during selection. $K_d$ and $Fb_{max}$ values are derived in Kaleidagraph by fitting the equation Fb = (Fbmax) * [thrombin]/($K_d$ + [thrombin]) to the plot of average triplicate Fb (fraction bound) data vs. thrombin concentration. Errors in the table are standard errors of the fitted parameters reported by Kaleidagraph's nonlinear curve fit function.

Example 7—Truncation of Clone 9 and Thrombin Affinity Measurements by BLI and Filter Binding The binding of immobilized truncated clone 9 to thrombin was examined in real time via biolayer interferometry (BLI) using a ForteBio BLItz instrument. Truncated RNA Clone 9 (see FIG. 2), modified with a 3'-15-atom triethylene glycol (TEG) spacer arm and biotin tag, was synthesized by IDT and immobilized on a streptavidin sensor. Association and dissociation of thrombin was observed at several concentrations (0.5, 1, 2, 4, 8, 16, and 32 nM). A new biosensor was used for each curve and reproducibility between sensors was achieved by integrating a preconditioning step prior to aptamer loading. Binding experiments were performed as follows: Each biosensor was hydrated in buffer 1 (20 mM Tris pH 7.5, 150 mM NaCl, 2 mM $MgSO_4$, 0.20 mg/mL BSA, 0.02% Tween-20) for 20 minutes. Shaker speed was maintained at 2600 rpm during the experiment. After loading the biosensor onto the instrument, a 30 s baseline in buffer 1 was followed by a 240s preconditioning step in Buffer 2 (50 mM NaOH, 1M NaOH). Equilibration of the biosensor in buffer 1 was achieved by two sequential 30s baselines in buffer 1. The aptamer was loaded during a 90s step in load buffer (Buffer 1 with 25 nM folded aptamer) yielding a response of 0.4 nm. Preassociation equilibration of the biosensor was achieved by two sequential 30s baseline measurements in buffer 3 (20 mM Tris pH 7.5, 150 mM NaCl, 2 mM $MgSO_4$, 2.0 mg/mL BSA, 0.1% v/v Tween-20). Association of thrombin in buffer 3 was monitored for 360s and dissociation was monitored in blank buffer 3 for 300s. All data was referenced against an aptamer-loaded sensor exposed to blank buffer to subtract the effect of buffer changes. Data were exported into Graphpad Prism and curve fit to a 1:1 binding model yielding rate constants of $k_{on}$=(91.9±0.1)×$10^4$ $M^{-1}$ $s^{-1}$ and $k_{off}$=(4.12±0.02)×$10^{-4}$ $s^{-1}$, corresponding to a $K_D$ of 448±2 µM. $R_{max}$ was globally fit, yielding a value of 1.477±0.001. Errors reported are the standard errors of the curve fit.

Equations Used in GPP:

Radioligand=HotNM*1e−9

Kob=[Radioligand]*Kon+Koff

Kd=Koff/Kon

Eq=R max*radioligand/(radioligand+Kd)

Association=Eq*(1−exp(−1*Kob*X))

YatTime0=Eq*(1−exp(−1*Kob*Time0))

Dissociation=YatTime0*exp(−1*Koff*(X−Time0))

Y=IF(X<Time0,Association,Dissociation)+NS

Discussion of Examples 1-7

Figures 3A, 3B:
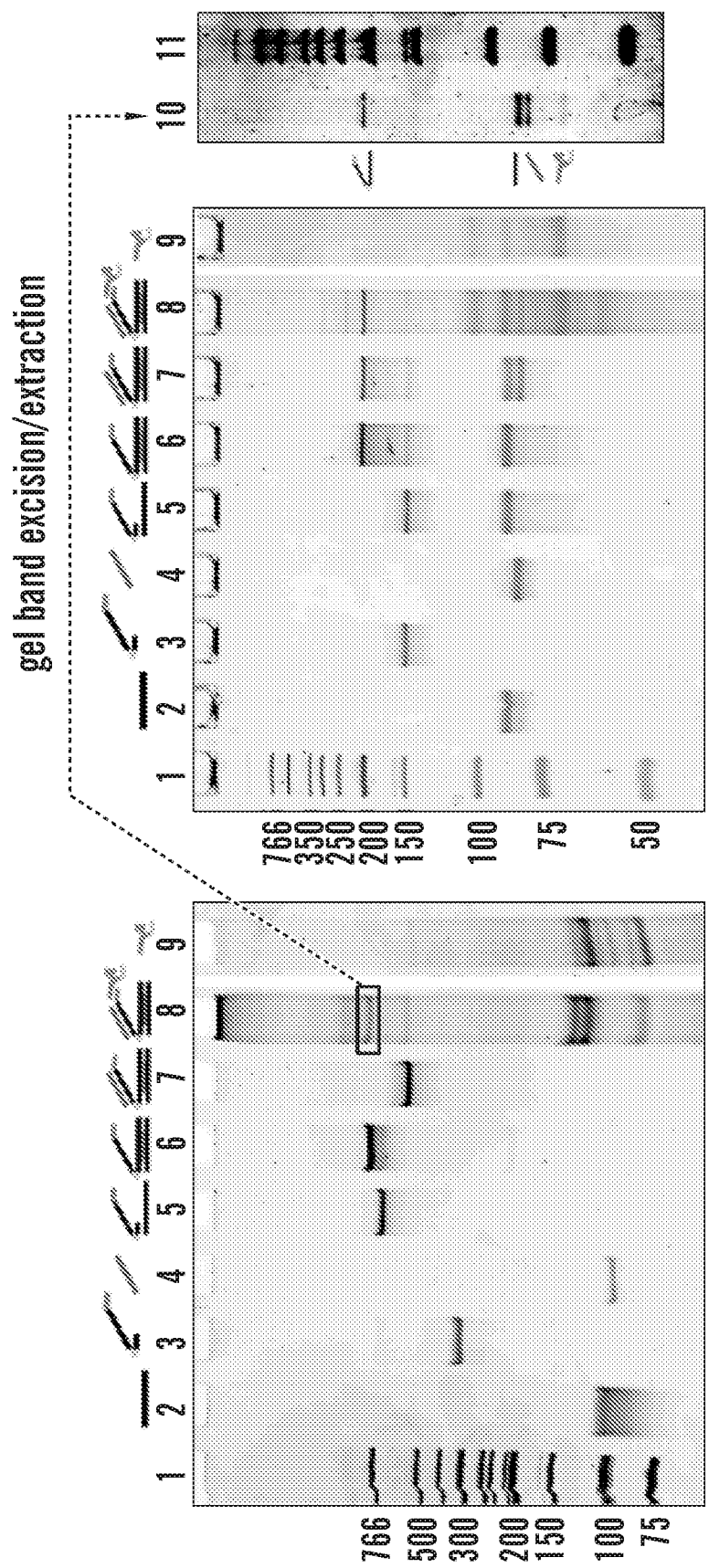
FIGS. 3A-B are images of non-denaturing (3A) and denaturing (3B) gels of library generation. In both gels, lanes 2-4 are controls that show migration of the individual purchased oligos; lanes 5-8 show the migration of species produced when these components are combined and used to generate the library; lane 9 is a control showing that RNA transcription of an ordinary DNA duplex produces several additional bands observed in lane 8. Lane contents: 1) LMW ladder (NEB); 2) non-coding library strand (10 pmol); 3) capture arm (10 pmol); 4) rigidifier (10 pmol); 5) library annealed to capture arm (0.25 pmol); 6) extension product, 0.25 pmol; 7) extension product annealed to rigidifier (0.25 pmol); 8) transcribed library (0.25 pmol) 9) transcribed library without capture arm. The box in FIG. 3A indicates the final RNA-displayed library, which was excised from the gel, eluted from the gel slice and rerun on a denaturing gel (FIG. 3B, lane 10).

FIG. 3 shows the various library species, as visualized in native (A) and denaturing (B) PAGE gels. For lanes 5-7, comparison of the two gels shows clearly that bands in the native gel corresponding to FIG. 1 species C, D, and E each separate into two or three strands of the appropriate size in the denaturing gel. The lane 8 band highlighted with a box in the native gel was hypothesized to be the DNA-displayed RNA species. To confirm this assignment, the band was excised from the native gel, and the material extracted from the gel slice was rerun on a denaturing gel (lane 10), giving rise to four bands matching the separate component strands. Extra bands in lane 8 show that library generation results in additional species, which were hypothesized to be excess RNA transcripts and other species resulting from transcription that do not anneal to the library. This was confirmed (lanes 9) by a control transcription of the DNA library lacking a capture arm (FIG. 1, Step A), which produced most of the bands present in Lane 8, but not the one attributed to the self-annealed RNA-DNA library, Step G (boxed band).

Figure 4A:
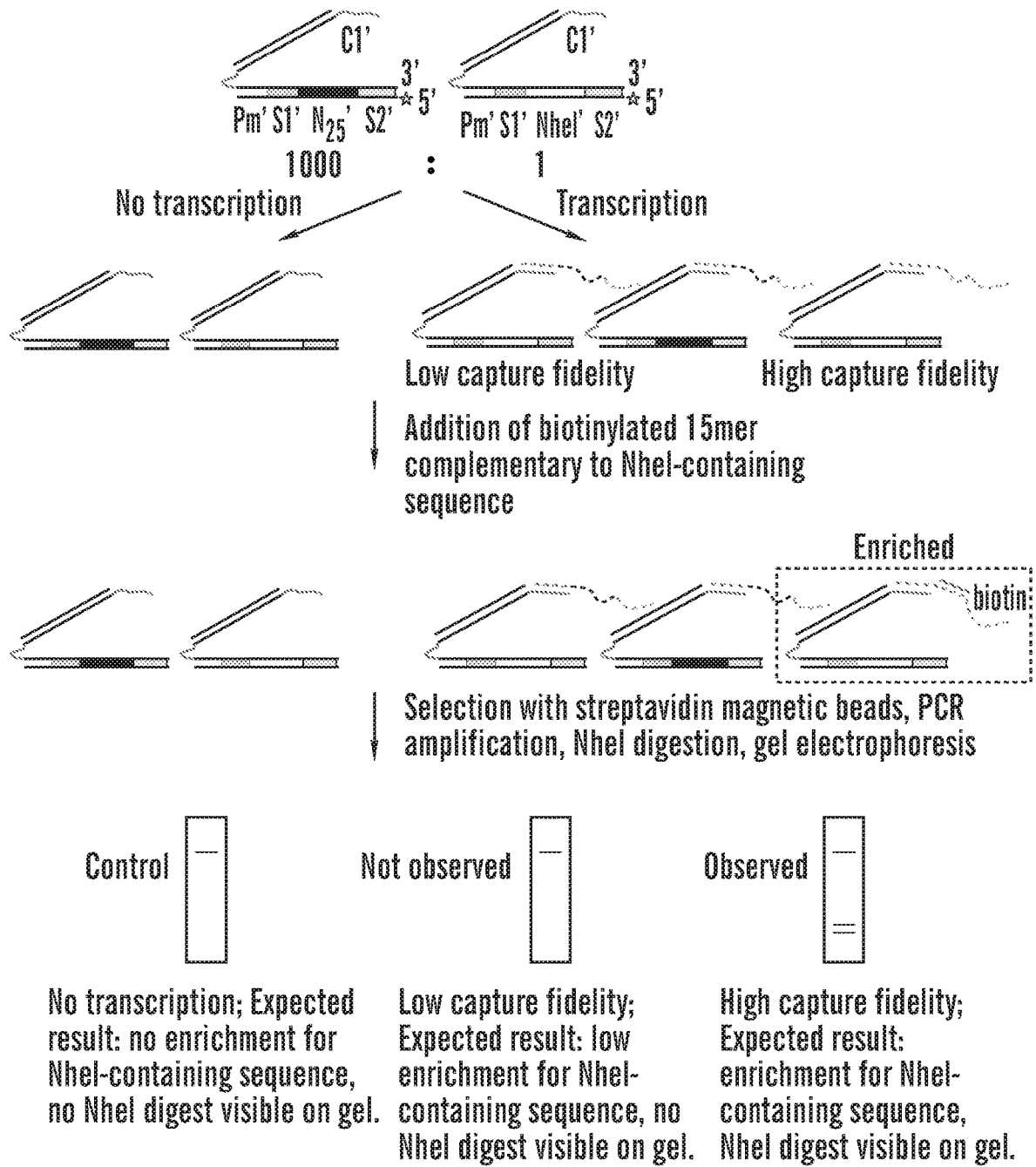
FIG. 4A is a schematic illustration of the faithful capture of RNA by its encoding DNA demonstrated by a simple hybridization-based selection.
Figure 4B:
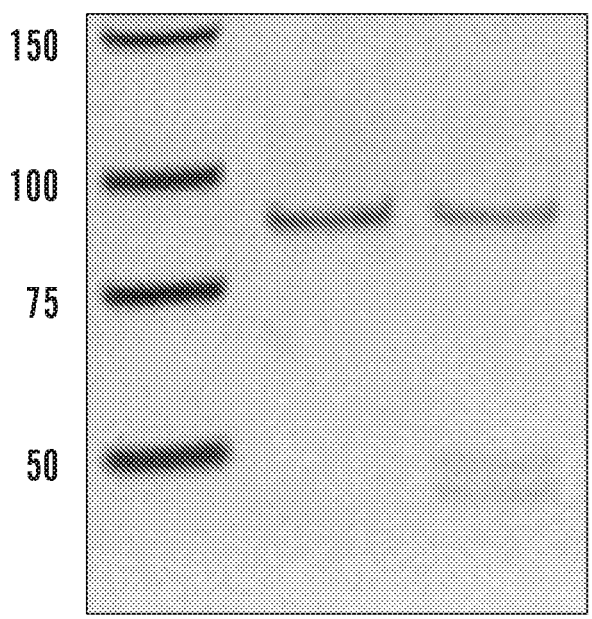
FIG. 4B is an image of a gel where Lane 1 contains a ladder; lane 2 contains the NheI-digested PCR amplicon from non-transcribed library (Control); and lane 3 contains the NheI-digested PCR amplicon from transcribed library. Amplifications in lanes 2 and 3 were performed on recovered library after the second round of selection.

To verify that the RNA transcript was being captured "intrastructurally" on its own DNA, with sufficient fidelity for selections, a proof-of-principle experiment was preformed to show that a sequence with known binding activity could be enriched from a spiked library. To this end, a random RNA-displayed DNA library spiked with 1:1000 of an NheI restriction site sequence was generated. After incubation of the library with a biotinylated DNA oligo complementary to the NheI sequence, the bound fraction was isolated with streptavidin magnetic beads and binders were amplified and regenerated. After two rounds of selection, a significant proportion of the recovered DNA contained the selected sequence (as evidenced by its NheI restriction susceptibility), indicating that the RNA was correctly captured by the DNA encoding it (FIGS. 4A-4B). To control for the possibility that the NheI-cleavable PCR product resulted from traces of the bait sequence contaminating the sample, a parallel selection was performed with the transcription step omitted. In this negative control, more PCR cycles were required to amplify selected library, and the resulting library was not susceptible to NheI cleavage.

With this evidence that the RNA library was effectively displayed on its encoding DNA, a more rigorous test of the system was attempted by using it to select RNA sequences that could bind to a protein. Human α-thrombin was chosen as a target. It is a commonly used target in proof-of-principle studies (Bock et al., Nature, 355:564-566 (1992), which is hereby incorporated by reference in its entirety). The library described above was prepared without the added NheI cleavage sequence and was then panned for binding to biotinylated thrombin over 10 rounds of selection with capture on streptavidin beads. Enrichment for binders was evident after the 7th round as indicated by the decreased number of PCR cycles required to recover the library. Stringency was then increased by lowering the thrombin concentration from 10 to 1 nM and shortening incubation time from 1 hour to 5 minutes; after the 10th round of selection the library was cloned and 10 members sequenced and analyzed for thrombin binding. As Table 1 indicates, all but two of the isolated sequences showed similarity in both sequence and predicted secondary structure.

Figure 2B:
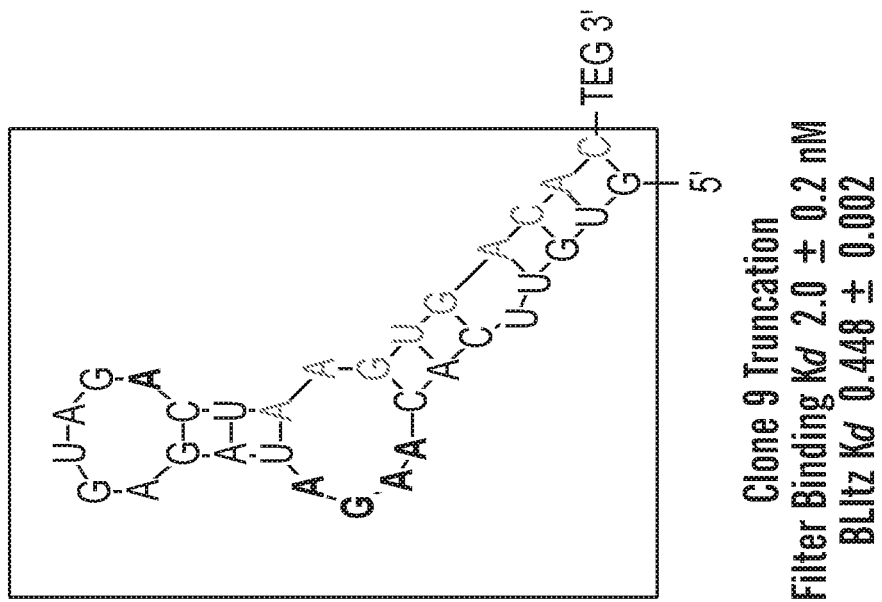
FIGS. 2A-D show truncated clone 9 thrombin affinity measurements by Biolayer Interferometry ("BLI") and filter binding.
Figure 2A:
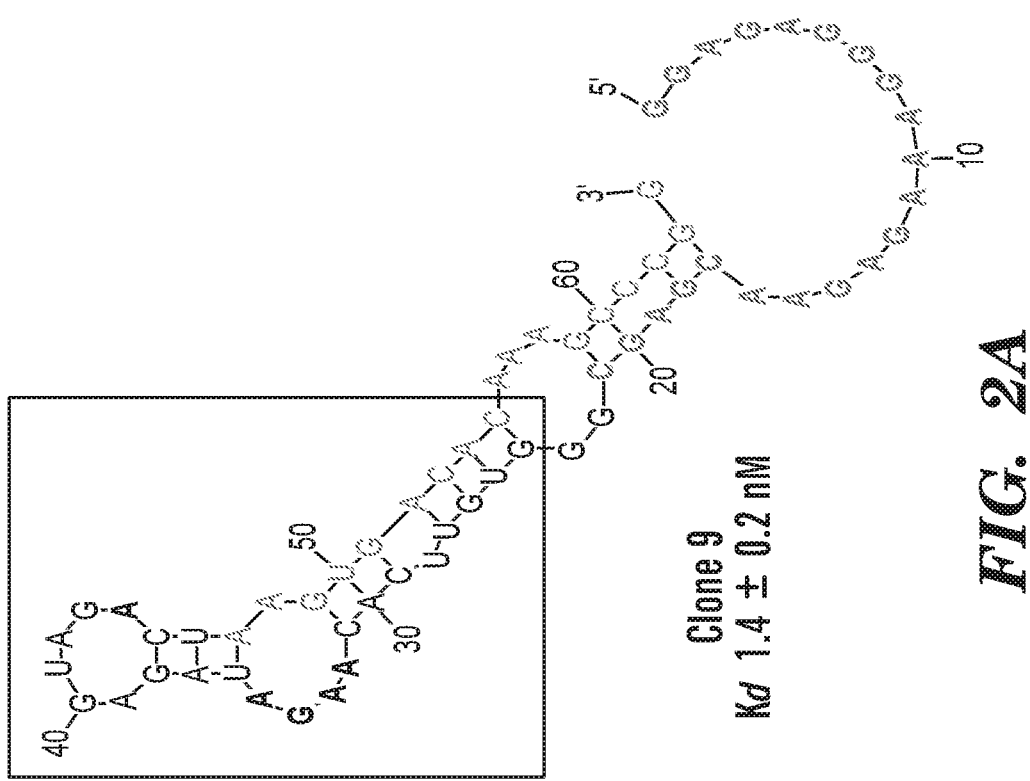
Figure 2C:
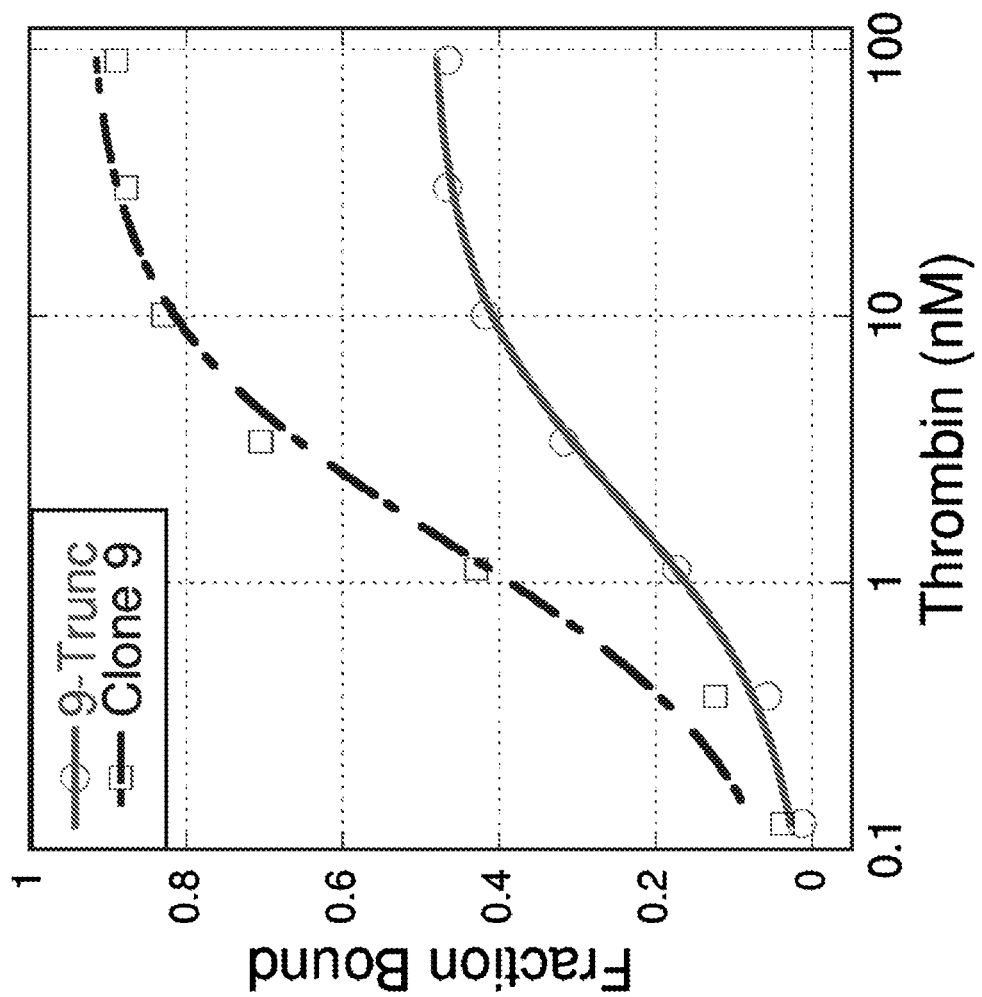
Figure 2D:
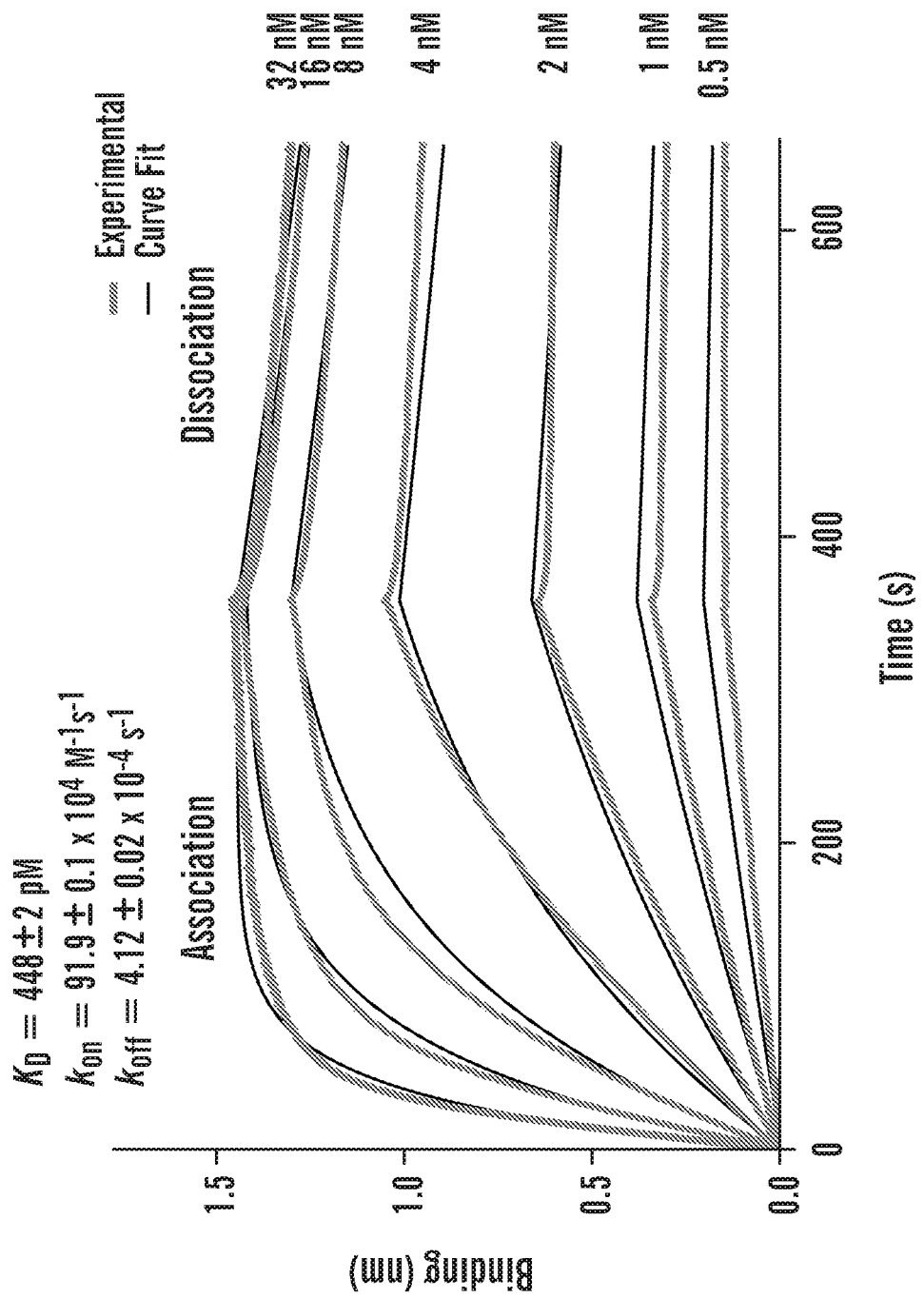

Thrombin binding affinity was measured for the corresponding RNAs of the 10 clones in nitrocellulose filter binding assays. For the eight related clones, dissociation constants (Table 1) ranged from 1.4 to 44.7 nM. Dissociation constants are derived from triplicate measurement in nitrocellulose filter binding assays, and the error reported is the standard error of the curve fit. Each oligo also contains 5' and 3' sequences complementary to the capture strand and reverse primer, respectively, which are presented together with binding curves for each clone in FIGS. 5A and 5B. Interestingly, the predicted RNA folds for these sequences, as determined by mFOLD, were strikingly similar to each other and to a previously isolated thrombin RNA aptamer for which a co-crystal structure (PDB ID 3DD2) has been obtained (Long et al., RNA, 14:2504-2512 (2008); White et al., Mol. Ther., 4:567-573 (2001), which are hereby incorporated by reference in their entirety). A prominent feature of the aptamer fold in the crystal structure is adenosine stacking, where the aptamer contains a stem motif followed by the bulge sequence AACA opposite a single adenosine, followed by another 3-base pair stem, 8 base loop structure. Two adenosines (ACA) in the bulge sequence (bold) sandwich an adenosine (bold) from the loop CUGAAGUA. The fourth adenosine also stacks against Arg233 of α-thrombin. In the aptamers obtained in the preceding Examples, a similar motif is found, where there is a bulge containing an AAXA opposite a lone adenosine (with the exception of clone 6, which contains AAXG opposite an adenosine), followed by a 3-base-pair stem, 6 base loop with a terminal adenosine in the otherwise variable loop. To confirm that the aptamers bind thrombin through their similar motif, a truncated variant of clone 9 was synthesized, containing only the portion highlighted in the box (FIG. 2B). Nitrocellulose filter binding and biolayer interferometry (BLI) measurements confirmed tight binding to thrombin (2 and 0.4 nM, respectively). Together, these data suggest that the aptamers adopt a conformation similar to those previously reported, and bind to the same region of thrombin, exosite II.

Figure 6:
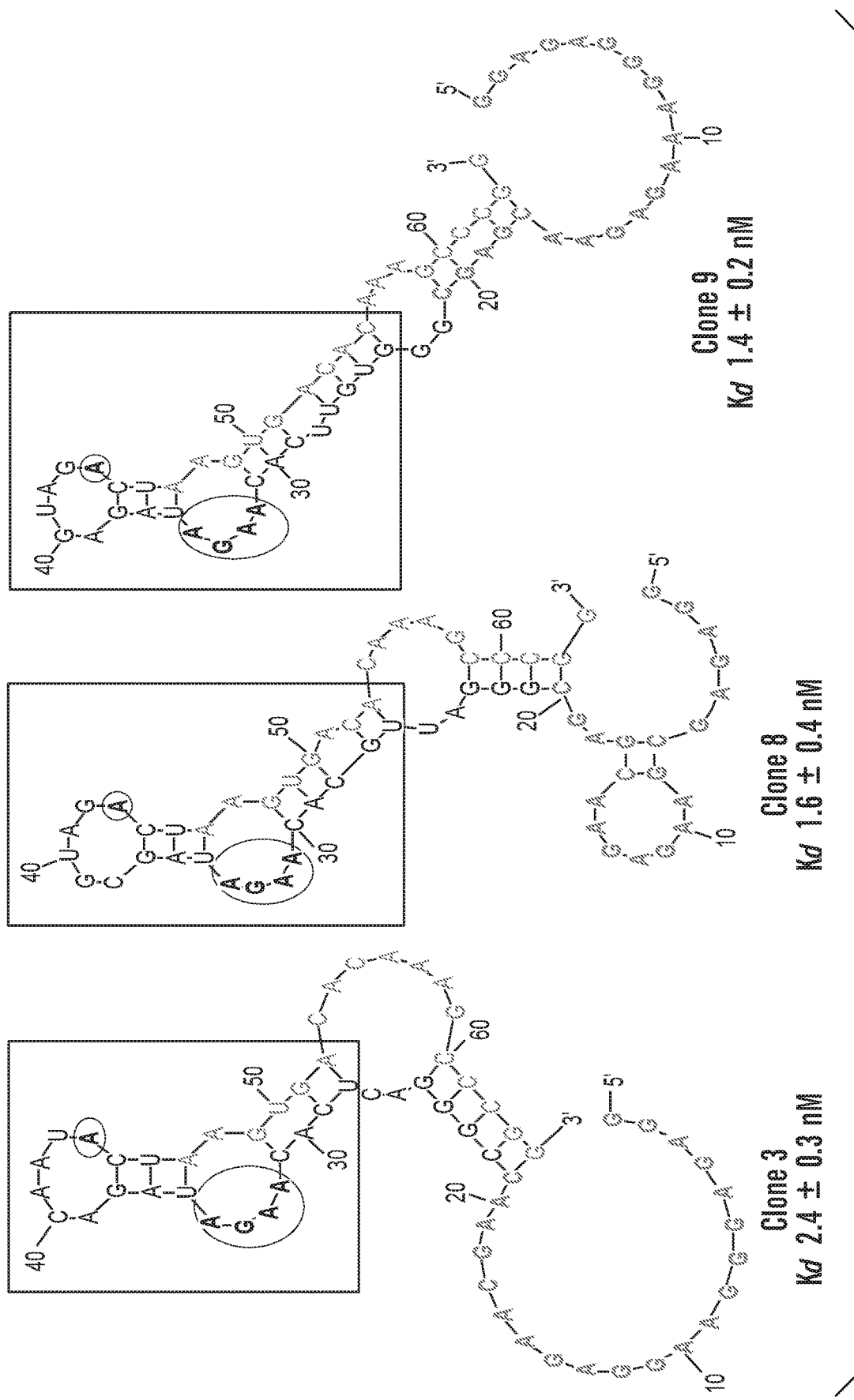
FIG. 6 shows mFold predictions of most stable secondary structures for clone 3 (SEQ ID NO: 22), clone 8 (SEQ ID NO: 27), and clone 9 (SEQ ID NO: 28) as well as clone 5 (SEQ ID NO: 24) and clone 7 (SEQ ID NO: 26). The boxes and circled letters highlight the stem loop structure and sequence common to most binding clones, and to the "Toggle 25" aptamer (SEQ ID NO: 30) previously reported by Sullenger and Long (Tanasova et al., *ChemBioChem*, 16:1212-1218 (2015); Zuker, M., *Nucleic Acids Res.*, 31:3406-3415 (2003), which are hereby incorporated by reference in their entirety). The 5' end through nt 20 or 21 indicates the capture strand complement, and the 3' end to nt 47 or 46 indicates the complement of the reverse primer.
Figure 6:
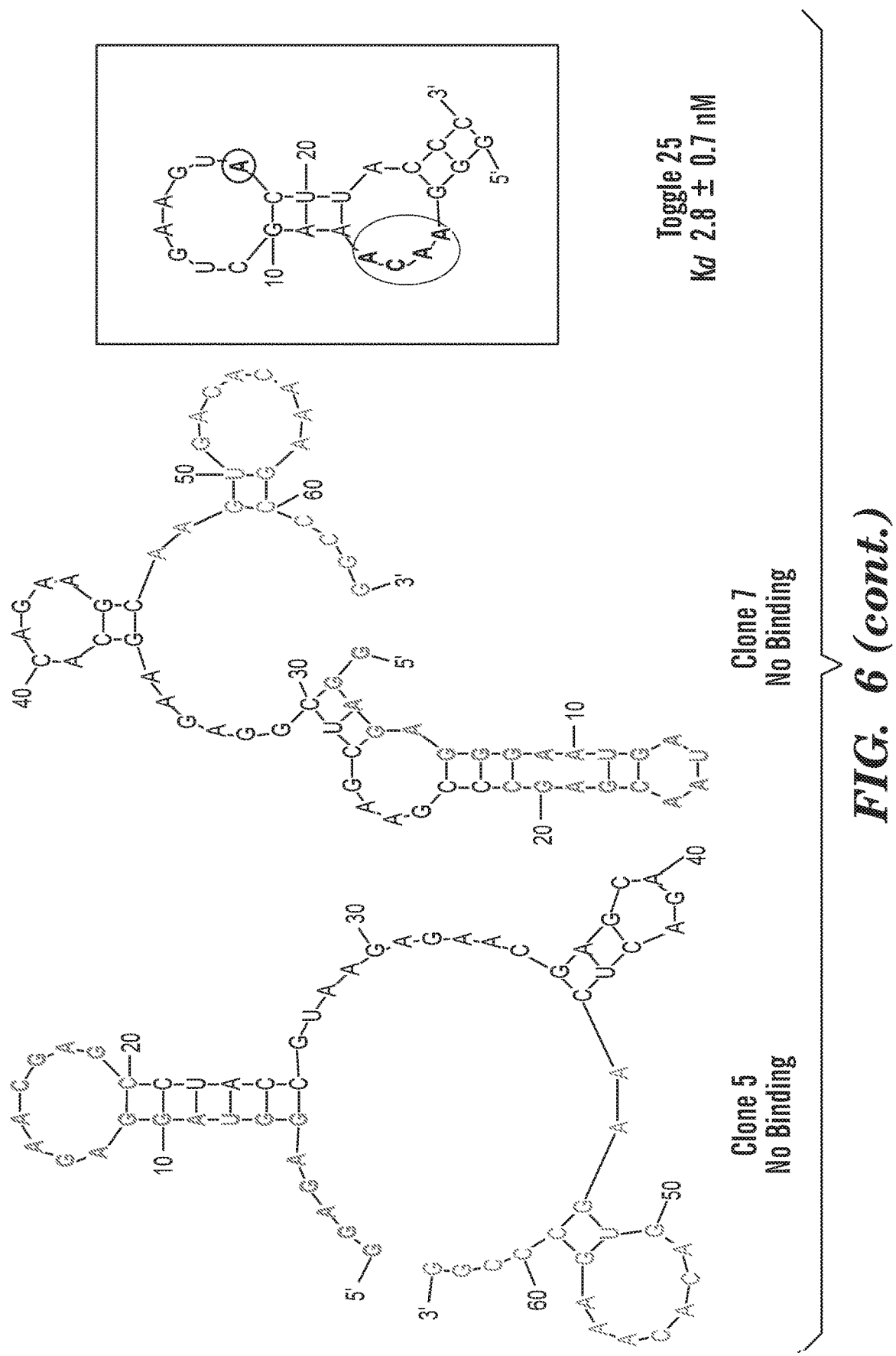

Little or no binding was detected for the remaining two sequences, clones 5 and 7. The predicted fold of clones 5 and 7 (FIG. 6) is such that the 5' capture strand complement region engages in extensive base pairing, which would be predicted to inhibit the capture of the RNA by the DNA and therefore render the DNA display ineffective for these clones. Because library generation produces excess free RNA transcripts, abundant thrombin-binding free RNA present in later rounds may anneal to DNA capture strands belonging to sequences such as 5 and 7 that are unable to self-capture, thereby rescuing them. Alternative explanations for the presence of non-binding sequences are that they are simply particularly efficient PCR substrates, or that they might bind to thrombin in a manner that is dependent on the presence of their DNA tag. Negative selection steps can therefore be used if non-binding sequences become prevalent.

In summary, the present application describes a verified method for DNA display of RNA. In the future, the benefits of using RNA in selections (structural diversity, amenability to 2' modifications for nuclease resistance) can be coupled with substantial post-transcriptional modification in a SELMA-type experiment (MacPherson et al., Angew. Chem., Int. Ed., 50:11238-11242 (2011), which is hereby incorporated by reference in its entirety). Applications other than SELMA may also benefit from DNA display of RNA. For instance, it will be useful in RNA-SELEX using unnatural NTPs that are accepted by T7 RNA polymerase, but then render the RNA a poor template for reverse transcriptase. It should be noted that the display method described herein uses commercially available enzymes and DNA oligonucleotide synthesis, and an entire library generation and selection cycle can be performed in a day.

Example 8—Synthesis of 5-ethynyl-2'-fluoro-2'-deoxyuridine-5'-triphosphate (2'F-EDUTP)

Synthesis of 5-ethynyl-2'-fluoro-2'-deoxyuridine-5'-triphosphate (2'F-EDUTP), 1, was carried out using the following procedures (Scheme 1 below) and reagents. All commercial reagents were used as provided unless otherwise indicated. Trimethyl phosphate and tributylamine were refluxed over $CaH_2$ and vacuum distilled into Schlenk flasks immediately before use. Phosphorus (V) oxychloride was refluxed and vacuum distilled into Schlenk flasks immediately use. Pyridine used for azeotropic drying was also freshly distilled from $CaH_2$. Triethylammonium bicarbonate buffer was prepared by bubbling $CO_2$ into a 1 M solution of triethylamine in water until homogenous solution at pH 8.0. $^1H$ NMR resonances are reported in ppm δ downfield of an external TMSP standard. $^{31}P$ NMR resonances are relative to an external $H_3PO_4$ standard, and $^{19}F$ NMR resonances are relative to an external trifluoroacetic acid standard.

Synthesis of 5-iodo-2'-fluoro-2'-deoxyuridine, 3, was performed using reaction conditions previously reported, starting with 2'-fluoro-2'-deoxyuridine, 2 (Paolini, et al., Synthesis 2003:1039-1042(2003), which is hereby incorporated by reference in its entirety).

Synthesis of 5-ethynyl-2'-fluoro-2'-deoxyuridine (2'F-EDU), 4, was performed using a previously reported method (MacPherson et al., Angew. Chem., Int. Ed., 50:11238-11242 (2011), which is hereby incorporated by reference in its entirety), starting with modified 5-iodo-2'-fluoro-2'-deoxyuridine instead of 5-iodo-2'deoxyuridine.

Scheme 1

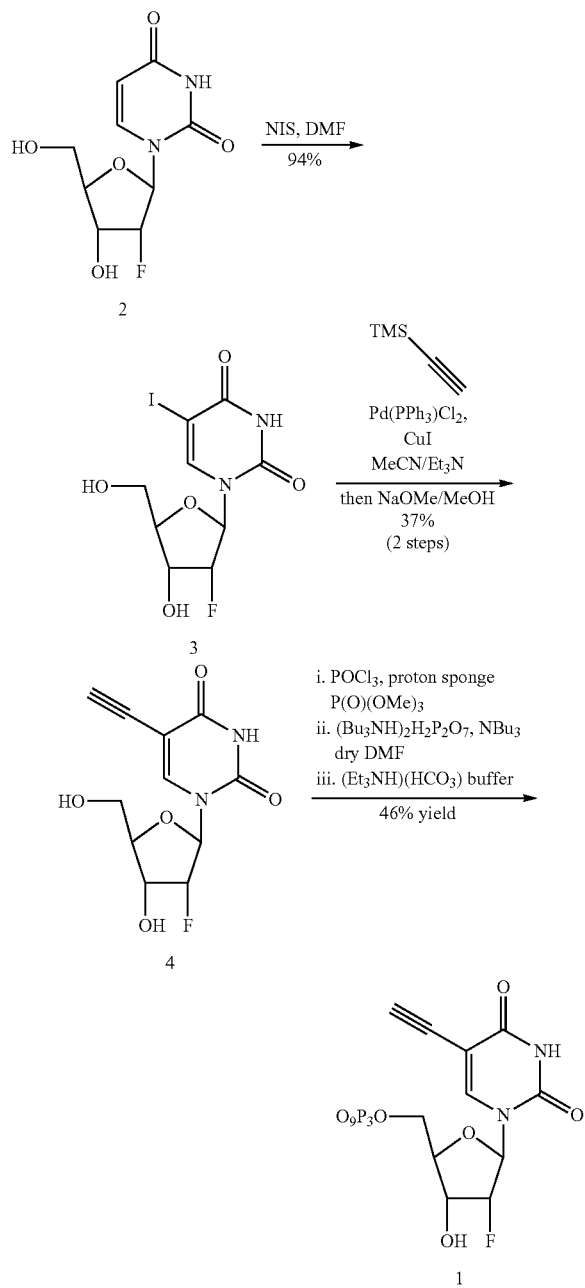

Synthesis of 5-ethynyl-2'-fluoro-2'-deoxyuridine-5'-triphosphate, 1, was performed as follows. 2'F-EDU (10 mg, 35 μmol) was dried by coevaporation with dry pyridine, and left over $P_2O_5$ in vacuo overnight. Proton sponge (48 mg, 225 μmol, 6.4 equiv.) was added and the mixture was dissolved in trimethyl phosphate (680 μL) under $N_2$ atmosphere. The magnetically stirred solution was cooled in an ice bath and dry $POCl_3$ (144, 150 μmol, 4.3 equiv.) was added dropwise via syringe. The reaction was monitored by TLC (6:3:1, iPrOH/$NH_4OH$/$H_2O$) for consumption of the starting material. After 75 min, a solution of tributylammonium pyrophosphate (160 mg, 290 μmol, 8.3 equiv.) and tributylamine (36 μL, 150 μmol, 4.3 equiv.) in dry DMF (160 μL), was added to the reaction. After 35 min, the reaction was quenched by adding the mixture dropwise into 4 mL of 0.2 M triethylammonium bicarbonate buffer. After 45 min of stirring on ice, this mixture was concentrated to dryness on a rotary evaporator. The mixture was redissolved in water (1 mL) and passed through a small column (6 cm×0.5 cm) of Dowex-$H^+$ 50WX8 ($Na^+$ form) to remove proton sponge. The fractions containing product (as indicated by negative ion ESI MS) were concentrated and purified by preparative HPLC (10×250 mm Waters XBridge prep C18 column, 5 μm, 130 Å, 4 mL/min) with a linear gradient of 2-15% B over 25 min, where B was 70% MeCN+aqueous 0.1M TEAB and A was aqueous 0.1M TEAB. Fractions containing product were again concentrated and redissolved in water then desalted by passage through a small column (6 cm×0.5 cm) of Dowex-$H^+$ 50WX8 ($Na^+$ form). Fractions containing product (as indicated by negative ion ESI MS) were combined and lyophilized to give the product as an off-white powder (8.2 mg, 41%). $^1$H NMR (400 MHz, $D_2O$) δ 8.18 (s, 1H, H-6), 6.06 (dd, J=18.4, 1.1 Hz, 1H, H-1'), 5.17 (dd, J=52.2, 4.7 Hz, 1H, H-2'), 4.54 (ddd, J=23.5, 8.6, 4.7 Hz, 1H, H-3'), 4.42-4.25 (m, 3H, H-4', H-5', H-5'), 3.56 (s, 1H, C≡CH). $^{19}$F NMR ($D_2O$) δ-202.84 (ddd, J=52.1, 23.5, 18.4 Hz). $^{31}$P NMR ($D_2O$) δ-6.33 (d, J=21.3 Hz), −11.15 (d, J=20.1), −22.19 (dd, J=21.3, 20.1 Hz).

Example 9—Library Construction for Incorporation of Modified Oligonucleotides

In general, the library design and intended use thereof for DNA-supported display of modified RNA libraries involves slightly modified reagents relative to those used in Examples 1-7. The modified reagents are shown in Table 5 below.

TABLE 5

Oligonucleotides Used for Modified RNA Display

| Name | Sequence | SEQ. ID NO |
|---|---|---|
| Random Library (Nonfluorinated) | CCGGGCTTTGTGTCACTT*NNNNNNNNNNNNNNNNNNNNNNNNNG* CTCGTTCTCCTTCCCTCTCCTATAGTGAGTCGTATTACAGTTG | 12 |
| Random Library (Fluorinated) | CCGGGCTTTGTGTCGCTT*NNNNNNNNNNNNNNNNNNNNNNNNNC* *TTCCTCTCCCTCTCCCTTCCTCTTCC*TCCTATAGTGAGTCGTAT TACAGTTG | 33 |

TABLE 5-continued

Oligonucleotides Used for Modified RNA Display

| Name | Sequence | SEQ. ID NO |
|---|---|---|
| Capture Strand (Nonfluorinated) | GCTCGTTCTCCTTCCCTCTCCTTTTTTTTTCAACACCACAGAC CAGTATACCCAGAAATGACGCAAGCATAGA<u>CAAACGATTTAGAC ATGAGTGCCCCACACAACGAACAAGC</u>TTTTTTTTTA-Z-CAACTGTAATACGACTCACTATAGGAGA | 31, 32 |
| Capture Strand (Fluorinated) | *CCTCTCCCTTCCTCTTCCTCC*TTTTTTTTTCAACACCACAGAC CAGTATACCCAGAAATGACGCAAGCATAGA<u>CAAACGATTTAGAC ATGAGTGCCCCACACAACGAACAAGC</u>TTTTTTTTTA-Z-CAACTGTAATACGACTCACTATAGGAGG | 34, 35 |

In Table 5, all oligonucleotides are shown in 5'-3' orientation. For the random library (SEQ ID NO: 33), the random sequence was not biased. For the capture strand, the rigidifier binding site is underlined, the capture sequence is in bold, and Z represents a hexaethyleneglycol spacer.

Briefly, in fluorinated library (SEQ ID NO: 33) the region (shown with bold/italics) between T7 promoter and the random region was extended (relative to non-fluorinated library of SEQ ID NO: 12) and designed to lack sequence that would transcribe fluorinated ribonucleotides (2'F-CTP, 2'F-EDUTP), allowing polymerase to begin transcription with natural ribonucleotides. The region located 3' to that shown in bold/italics is the capture strand primer annealing site. In addition, the capture strand was also modified at its 5' end (relative to the non-fluorinated capture strand) so that its RNA capture sequence differed.

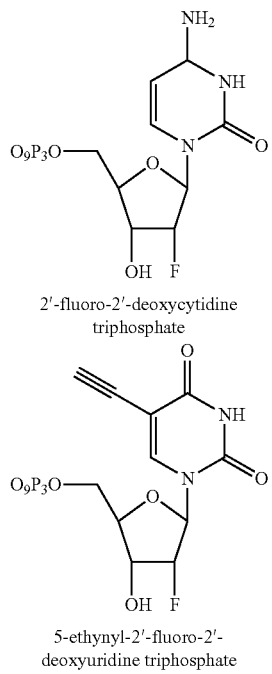

2'-fluoro-2'-deoxycytidine triphosphate 5-ethynyl-2'-fluoro-2'-deoxyuridine triphosphate In the procedure described in Example 1, modified rNTPs will be incorporated into the reaction medium with T7 R&DNA polymerase. CTP will be replaced by a modified 2'-fluoro-2'-deoxycytidine triphosphate, while UTP will be replaced with a modified 5-ethynyl-2'-fluoro-2'-deoxyuridine triphosphate. The incorporation of 2'-fluoro-2'-deoxypyrimidines in the RNA strand are expected to result in superior stability and resistance towards RNAse A digestion. T7 R&DNA polymerase will allow for the efficient incorporation of 2'-deoxynucleotide triphosphates into the synthesized RNA strand. T7 R&DNA polymerase is also able to incorporate 5-ethynyl pyrimidines, which can then be utilized with CuAAC "click" chemistry (see MacPherson et al., *Angew. Chem., Int. Ed.*, 50:11238-11242 (2011), which is hereby incorporated by reference in its entirety).

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. All of the features described herein (including any accompanying claims, abstract and drawings), and/or all of the steps of any method or process so disclosed, may be combined with any of the above aspects in any combination, except combinations where at least some of such features and/or steps are mutually exclusive. Additionally, the recited order of processing elements or sequences, or the use of numbers, letters, or other designations therefore, is not intended to limit the claimed processes to any order except as may be specified in the claims. These alterations, improvements, and modifications are intended to be suggested hereby, and are within the spirit and scope of the invention. Accordingly, the invention is limited only by the following claims and equivalents thereto.

What is claimed:

1. A method for selecting RNA aptamers that bind to a target molecule without reverse transcription, comprising:
providing a pool of oligonucleotide complexes that each comprise a ds-DNA molecule, an RNA molecule encoded by the ds-DNA molecule, and a rigidifier oligonucleotide, wherein a capture strand linked to the ds-DNA molecule is partially annealed to the RNA molecule via a 5' capture region in the RNA molecule which is complementary to a complementary region of the capture strand, and wherein a Tm between the annealed 5' capture region in the RNA molecule and the capture strand is at least 60° C.,
wherein the ds-DNA molecule comprises a coding strand and a complementary non-coding strand which encode the RNA molecule,
wherein the coding strand comprises an RNA coding portion, and wherein a linker molecule tethers the 3' end of the capture strand to the 5' end of the RNA coding portion, wherein the capture strand comprises, 3' to 5', a rigidifiable region and the complementary region to the capture region in the RNA molecule, wherein the rigidifier oligonucleotide is complementary to the rigidifiable region and increases the likelihood that the 5' capture region in the RNA molecule and the capture strand hybridize,
wherein the ds-DNA molecule comprises an operably linked promoter sequence for transcription of the RNA molecule, a primer binding site at the 3' end of the non-coding strand, and a primer binding site at the 3' end of the coding strand;
wherein the non-coding strand comprises a non-natural deoxynucleotide base at the 5' end of the non-coding strand, wherein the non-natural deoxynucleotide base stalls RNA polymerase and facilitates annealing of the 5' capture region in the RNA molecule to the capture strand;
wherein the RNA molecule comprises at the 3' end of the 5' capture region a nucleotide sequence that forms a secondary structure when the 3' end of the RNA molecule is free;
exposing the pool to the target molecule and allowing the RNA molecule that has formed a secondary structure at the 3' end of the 5' capture region to bind the target molecule to provide a pool of selected oligonucleotide complexes which bind the target molecule; and
selecting the RNA aptamers from the pool of selected oligonucleotide complexes wherein the selected RNA aptamers are bound to the target molecule.

2. The method according to claim 1, wherein the linker molecule is selected from the group consisting of hexaethyleneglycol, polyethylene glycol, an aliphatic hydrocarbon, and a peptide.

3. The method according to claim 1, wherein the RNA molecule comprises one or more modified nucleotides or modified ribosyl-phosphate groups.

4. The method according to claim 3, wherein the one or more modified nucleotides are selected from the group consisting of 2'-fluoro-ribonucleotides, 2'-amino-ribonucleotides, 2'-O-methyl-ribonucleotides, 5'-iodo-ribonucleotides, 5'-bromo-ribonucleotides, and alkyne-modified ribonucleotides.

5. The method according to claim 3, wherein the modified ribosyl-phosphate groups comprise a phosphorothioate-linked nucleotide.

6. The method according to claim 1, wherein the method further comprises:
amplifying the pool of selected oligonucleotide complexes using a biotinylated forward primer that binds to the primer binding site at the 3' end of the non-coding strand and a reverse primer comprising a non-natural deoxynucleotide base that binds to the primer binding site at the 3' end of the coding strand; and
recovering the amplified pool of selected oligonucleotide complexes,
wherein amplifying does not include reverse transcription.

7. The method according to claim 6, further comprising using the amplified pool of selected oligonucleotide complexes to prepare a first selected ds-DNA molecule, the method comprising
removing the coding strand from the amplified pool of selected oligonucleotide complexes,
annealing the capture strand to the primer binding site at the 3' end of the coding strand, wherein the capture strand comprises a reverse primer that binds to the primer binding site at the 3' end of the coding strand and a sequence complementary to the DNA capture arm, and
adding a DNA polymerase in the presence of dNTPs under conditions effective to extend the reverse primer sequence to provide the first selected ds-DNA molecule comprising a selected coding strand and a complementary selected non-coding strand which encode the RNA aptamers.

8. The method according to claim 7, further comprising:
transcribing the first selected ds-DNA molecule using an RNA polymerase and rNTP's under conditions effective to form a second pool of oligonucleotide complexes that each comprise a first selected ds-DNA molecule and a second round RNA molecule, encoded by the first selected ds-DNA molecule, wherein the capture DNA arm of the ds-DNA molecule is at least partially annealed to the second round RNA molecule via a 5' RNA capture region in the second round RNA molecule which is complementary to the DNA capture arm, and wherein a Tm of the annealed capture region is at least 60° C.

9. The method according to claim 8, wherein the rNTP's comprise one or more modified bases or ribosyl-phosphate groups.

10. The method according to claim 9, wherein the one or more modified bases are selected from the group consisting of 2'-fluoro-rNTP, 2'-amino-rNTP, 2'-O-methyl-rNTP, 5'-iodo-rNTP, 5'-bromo-rNTP, alkyne-modified rNTP.

11. The method according to claim 9, wherein the modified ribosyl-phosphate groups comprise a phosphorothioate-linked nucleotide.

12. The method according to claim 8, further comprising:
exposing the second pool of oligonucleotide complexes to the target molecule and allowing the second round RNA molecule to bind the target molecule, wherein the second round RNA molecule comprises a nucleotide sequence that forms a secondary structure when the 3' end of the RNA molecule is free; and
selecting from the second pool one or more oligonucleotide complexes comprising second round RNA aptamers having the secondary structure bound to the target molecule.

13. The method according to claim 12, further comprising:
obtaining additional rounds of RNA molecules comprising repeating, one or more times, the method steps of said amplifying the pool of selected oligonucleotide complexes, said recovering the amplified pool of selected oligonucleotide complexes, said removing the coding strand, said annealing the capture strand, said adding the DNA polymerase, and transcribing the selected ds-DNA molecule to form additional pools of oligonucleotide complexes;
exposing the additional pools to the target molecule and allowing the RNA molecules to bind the target molecule, wherein each of the RNA molecules comprises a nucleotide sequence that forms a secondary structure when the 3' end of the RNA molecule is free; and
selecting from the additional pools one or more oligonucleotide complexes comprising the RNA aptamers having the secondary structure bound to the target molecule.

14. The method according to claim 1, wherein the linker molecule is a nucleotide spacer molecule comprising a plurality of mismatches at the 3' end of the non-coding strand such that the nucleotide spacer molecule linker does not base pair with the coding strand.

* * * * *